(12) United States Patent  
Eggers et al.

(10) Patent No.: US 6,322,549 B1  
(45) Date of Patent: Nov. 27, 2001

(54) SYSTEMS AND METHODS FOR ELECTROSURGICAL TREATMENT OF TISSUE IN THE BRAIN AND SPINAL CORD

(75) Inventors: Philip E. Eggers, Dublin, OH (US); Hira V. Thapliyal, Los Altos, CA (US)

(73) Assignee: ArthoCare Corporation, Sunnyvale, CA (US)

(*) Notice: Subject to any disclaimer, the term of this patent is extended or adjusted under 35 U.S.C. 154(b) by 0 days.

(21) Appl. No.: 09/478,729

(22) Filed: Jan. 6, 2000

Related U.S. Application Data

(63) Continuation-in-part of application No. 09/026,851, filed on Feb. 20, 1998, now Pat. No. 6,277,112.

(51) Int. Cl.[7] ..................................................... A61M 31/00
(52) U.S. Cl. ............................................. 604/500; 604/114
(58) Field of Search ................................. 604/28, 43, 114, 604/500, 518, 522, 22; 606/35–42

(56) References Cited

U.S. PATENT DOCUMENTS

| | | |
|---|---|---|
| 2,050,904 | 8/1936 | Trice . |
| 4,033,351 | 7/1977 | Hetzel ................................. 128/303 |
| 4,040,426 | 8/1977 | Morrison, Jr. ....................... 128/303 |
| 4,043,342 | 8/1977 | Morrison, Jr. ....................... 128/303 |
| 4,116,198 | 9/1978 | Roos .................................... 128/303 |
| 4,184,492 | 1/1980 | Meinke et al. ...................... 128/303 |
| 4,202,337 | 5/1980 | Hren et al. .......................... 128/303 |
| 4,228,800 | 10/1980 | Degler, Jr. et al. ................. 128/303 |
| 4,232,676 | 11/1980 | Herczog .............................. 128/303 |

(List continued on next page.)

FOREIGN PATENT DOCUMENTS

| | | | |
|---|---|---|---|
| 0 740 926 | 11/1996 | (EP) | ............................... A61B/17/39 |
| 0 754 437 | 1/1997 | (EP) | ............................... A61B/17/39 |
| 0 703 461 | 3/1996 | (EP) | ............................... G01R/27/02 |
| 2 308 979 | 7/1997 | (GB) . | |
| 2 308 980 | 7/1997 | (GB) . | |
| 2 308 981 | 7/1997 | (GB) . | |

(List continued on next page.)

OTHER PUBLICATIONS

V.E. Elsasser et al. *Acta Medicotechnica* 24(4):129–134 (1976).
C. Slager et al. (1985) *JACC* 5(6):1382–6.
M. Buchelt et al. *Lasers In Surgery and Medecine* 11:271–279 (1991).
J. Costello *Lasers in Surgery and Medicine* 12:121–124 (1992).

(List continued on next page.)

*Primary Examiner*—Richard K. Seidel
*Assistant Examiner*—Kevin C. Sirmons
(74) *Attorney, Agent, or Firm*—John T. Raffle

(57) ABSTRACT

The present invention provides systems and methods for selectively applying electrical energy to a target location within a patient's brain and spinal cord. The systems and methods of the present invention are particularly useful for treating cerebrovascular diseases, such as vessel occlusion, or for the volumetric removal or ablation of intracranial tumors or Arteriovenous Malformations (AVMs). The method of the present invention comprises positioning an electrosurgical probe or catheter adjacent the target site so that one or more electrode terminal(s) are brought into at least partial contact or close proximity with a body structure within the patient's head or neck, such as tumor tissue or an occlusion within a blood vessel. High frequency voltage is then applied between the electrode terminal(s) and one or more return electrode(s) to volumetrically remove or ablate at least a portion of the body structure in situ. In specific embodiments, the high frequency voltage is sufficient to effect the dissociation or disintegration of organic molecules into non-viable atoms and molecules. Specifically, the present invention converts the solid tissue cells into non-condensable gases that are no longer intact or viable, and thus, not capable of spreading viral or bacterial particles to other portions of the body structure.

29 Claims, 20 Drawing Sheets

U.S. PATENT DOCUMENTS

| | | | |
|---|---|---|---|
| 4,248,231 | 2/1981 | Herczog et al. | 128/303 |
| 4,326,529 | 4/1982 | Doss et al. | 128/303 |
| 4,381,007 | 4/1983 | Doss | 128/303 |
| 4,476,862 | 10/1984 | Pao | 128/303 |
| 4,532,924 | 8/1985 | Auth et al. | 128/303 |
| 4,548,207 | 10/1985 | Reimels | 128/303 |
| 4,567,890 | 2/1986 | Ohta et al. | 128/303 |
| 4,593,691 | 6/1986 | Lindstrom et al. | 128/303 |
| 4,674,499 | 6/1987 | Pao | 128/303 |
| 4,682,596 | 7/1987 | Bales et al. | 128/303 |
| 4,706,667 | 11/1987 | Roos | 128/303 |
| 4,765,331 | 8/1988 | Petruzzi et al. | 128/303 |
| 4,823,791 | 4/1989 | D'Amelio et al. | 123/303 |
| 4,860,752 | 8/1989 | Turner | 128/422 |
| 4,931,047 | 6/1990 | Broadwin et al. | 604/22 |
| 4,936,301 | 6/1990 | Rexroth et al. | 606/45 |
| 4,943,290 | 7/1990 | Rexroth et al. | 606/45 |
| 4,967,765 | 11/1990 | Turner et al. | 128/785 |
| 4,976,711 | 12/1990 | Parins et al. | 606/48 |
| 4,979,948 | 12/1990 | Geddes et al. | 606/33 |
| 4,998,933 | 3/1991 | Eggers et al. | 606/41 |
| 5,007,908 | 4/1991 | Rydell | 606/47 |
| 5,009,656 | 4/1991 | Reimels | 606/48 |
| 5,057,105 | 10/1991 | Malone et al. | 606/28 |
| 5,057,106 | 10/1991 | Kasevich et al. | 606/33 |
| 5,078,717 | 1/1992 | Parins et al. | 606/48 |
| 5,080,660 | 1/1992 | Buelna | 606/48 |
| 5,083,565 | 1/1992 | Parins | 128/642 |
| 5,098,431 | 3/1992 | Rydell | 606/48 |
| 5,108,391 | 4/1992 | Flachenecker | 606/38 |
| 5,112,330 | 5/1992 | Nishigaki et al. | 606/46 |
| 5,122,138 | 6/1992 | Manwaring | 606/46 |
| 5,125,928 | 6/1992 | Parins et al. | 606/48 |
| 5,178,620 | 1/1993 | Eggers et al. | 606/41 |
| 5,190,517 | 3/1993 | Zieve et al. | 604/22 |
| 5,195,959 | 3/1993 | Smith | 604/34 |
| 5,197,963 | 3/1993 | Parins | 606/46 |
| 5,213,580 | 5/1993 | Slepian et al. | 623/1 |
| 5,217,457 | 6/1993 | Delahuerga et al. | 606/42 |
| 5,249,585 | 10/1993 | Turner et al. | 607/99 |
| 5,267,994 | 12/1993 | Gentelia et al. | 606/15 |
| 5,267,997 | 12/1993 | Farin et al. | 606/38 |
| 5,273,524 | 12/1993 | Fox et al. | 604/21 |
| 5,277,201 | 1/1994 | Stern | 607/98 |
| 5,281,216 | 1/1994 | Klicek | 606/42 |
| 5,281,218 | 1/1994 | Imran | 606/41 |
| 5,290,282 | 3/1994 | Casscells | 606/29 |
| 5,300,069 | 4/1994 | Hunsberger et al. | 606/37 |
| 5,312,400 | 5/1994 | Bales et al. | 606/41 |
| 5,314,406 | 5/1994 | Arias et al. | 604/21 |
| 5,318,564 | 6/1994 | Eggers | 606/47 |
| 5,324,254 | 6/1994 | Phillips et al. | 604/21 |
| 5,328,471 | 7/1994 | Slepian | 604/101 |
| 5,330,470 | 7/1994 | Hagen | 606/42 |
| 5,334,140 | 8/1994 | Phillips | 604/35 |
| 5,334,183 | 8/1994 | Wuchinich | 606/46 |
| 5,336,220 | 8/1994 | Ryan et al. | 604/22 |
| 5,342,357 | 8/1994 | Nardella | 606/40 |
| 5,366,443 | 11/1994 | Eggers et al. | 604/114 |
| 5,370,675 | 12/1994 | Edwards et al. | 607/101 |
| 5,380,277 | 1/1995 | Phillips | 604/33 |
| 5,383,917 | 1/1995 | Desai et al. | 607/702 |
| 5,395,312 | 3/1995 | Desai | 604/22 |
| 5,417,687 | 5/1995 | Nardella et al. | 606/32 |
| 5,419,767 | 5/1995 | Eggers et al. | 604/114 |
| 5,439,446 | * 8/1995 | Barry | 604/96 |
| 5,454,809 | 10/1995 | Janssen | 606/41 |
| 5,562,703 | 10/1996 | Desai | 606/210 |
| 5,569,242 | 10/1996 | Lax et al. | 606/42 |
| 5,575,815 | 11/1996 | Slepian et al. | 623/1 |
| 5,609,151 | 3/1997 | Mulier et al. | 128/642 |
| 5,647,869 | 7/1997 | Goble et al. | 606/37 |
| 5,662,609 | 9/1997 | Slepian | 604/101 |
| 5,662,680 | 9/1997 | Desai | 606/210 |
| 5,674,287 | 10/1997 | Slepian et al. | 623/11 |
| 5,681,282 | 10/1997 | Eggers et al. | 604/114 |
| 5,683,366 | 11/1997 | Eggers et al. | 604/114 |
| 5,685,847 | 11/1997 | Barry | 604/96 |
| 5,697,281 | 12/1997 | Eggers et al. | 604/114 |
| 5,697,536 | 12/1997 | Eggers et al. | 604/114 |
| 5,697,882 | 12/1997 | Eggers et al. | 604/114 |
| 5,697,909 | 12/1997 | Eggers et al. | 604/114 |
| 5,700,262 | 12/1997 | Acosta | 606/48 |
| 5,725,524 | 3/1998 | Mulier et al. | 606/41 |
| 5,749,894 | 5/1998 | Engelson | 606/213 |
| 5,749,915 | 5/1998 | Slepian | 623/1 |
| 5,749,922 | 5/1998 | Slepian et al. | 623/1 |
| 5,766,153 | 6/1998 | Eggers et al. | 604/114 |
| 5,772,627 | 6/1998 | Acosta et al. | 604/22 |
| 5,800,538 | 9/1998 | Slepian et al. | 623/11 |
| 5,807,306 | * 9/1998 | Shapland et al. | 604/21 |
| 5,810,764 | * 9/1998 | Eggers et al. | 604/23 |
| 5,820,580 | * 10/1998 | Edwards et al. | 604/22 |
| 5,843,019 | * 12/1998 | Eggers et al. | 604/22 |
| 5,843,156 | 12/1998 | Slepian et al. | 623/1 |
| 5,857,998 | 1/1999 | Barry | 604/96 |
| 5,914,345 | 6/1999 | Slepian et al. | 514/496 |
| 5,941,869 | * 8/1999 | Patterson et al. | 604/508 |
| 5,947,977 | 9/1999 | Slepian et al. | 606/1 |
| 6,014,584 | * 1/2000 | Hofmann et al. | 604/21 |
| 6,036,681 | * 3/2000 | Hooven | 604/506 |

FOREIGN PATENT DOCUMENTS

| | | | |
|---|---|---|---|
| 2327350 | 1/1999 | (GB) | A61B/17/39 |
| 2327351 | 1/1999 | (GB) | A61B/17/39 |
| 2327352 | 1/1999 | (GB) | A61B/17/39 |
| 57-117843 | 7/1982 | (JP) | A61B/17/39 |
| WO 97/00070 | 1/1908 | (WO) | A61B/17/36 |
| WO 93/13816 | 7/1993 | (WO) | A61B/17/36 |
| WO 90/07303 | 7/1990 | (WO) | A61B/17/39 |
| 96/00042 | 1/1996 | (WO) | A61B/17/39 |
| WO 97/00646 | 1/1997 | (WO) | A61B/17/39 |
| WO 97/00647 | 1/1997 | (WO) | A61B/17/39 |
| 97/24073 | 7/1997 | (WO) | A61B/17/39 |
| 97/24993 | 7/1997 | (WO) | A61B/17/39 |
| 97/24994 | 7/1997 | (WO) | A61B/17/39 |
| 97/48346 | 12/1997 | (WO) | A61B/17/39 |
| WO 93/20747 | 10/1993 | (WO) | A61B/5/00 |
| WO 92/21278 | 12/1992 | (WO) | A61B/5/04 |
| WO 94/08654 | 4/1994 | (WO) | A61M/37/00 |
| WO 94/04220 | 3/1994 | (WO) | A61N/1/06 |

OTHER PUBLICATIONS

R. Tucker et al., Abstract P14–11, p. 248, "A Bipolar Electrosurgical Turp Loop".

R. Tucker et al. *J. of Urology* vol. 141, pp. 662–665, (1989).

R. Tucker et al. *Urological Research* vol. 18, pp. 291–294 (1990).

J. Saal et al. *NASS–APS First Joint Meeting*, Charleston SC, Apr. 1998.

E.V. Kramolowsky et al. *J. of Urology* vol. 143, pp. 275–277 (1990).

J.W. Ramsey et al. *Urological Research* vol. 13, pp. 99–102 (1985).

E. Kramolowsky et al. (1991) *J. of Urology* 146:669–674.

P.C. Nardella (1989) *SPIE* 1068:42–49.

Rand et al. (1985) *J. Arthro. Surg.* 1:242–246.

* cited by examiner

SYSTEMS AND METHODS FOR ELECTROSURGICAL TREATMENT OF TISSUE IN THE BRAIN AND SPINAL CORD

RELATED APPLICATIONS

The present application is a continuation-in-part of U.S. patent application Ser. No. 09/026,851, filed Feb. 20, 1998, now U.S. Pat. No. 6,277,112 the complete disclosure of which is incorporated herein by reference for all purposes. The application also derives priority from U.S. patent application Ser. No. 08/795,686, filed Nov. 22, 1995, the complete disclosure of which is incorporated herein by reference for all purposes.

The present invention is related to commonly assigned co-pending U.S. patent application Ser. No. 08/990,374, filed Dec. 15, 1997, which is a continuation-in-part of U.S. patent application Ser. No. 08/485,219, filed on Jun. 7, 1995, now U.S. Pat. No. 5,697,281, patent application Ser. Nos. 09/109,219, 09/058,571, 08/874,173 and 09/002,315, filed on Jun. 30, 1998, Apr. 10, 1998, Jun. 13, 1997, and Jan. 2, 1998, respectively and U.S. patent application Ser. No. 09/054,323, filed on Apr. 2, 1998, U.S. patent application Ser. No. 09/010,382, filed Jan. 21, 1998, and U.S. patent application Ser. No. 09/032,375, filed Feb. 27, 1998, U.S. patent application Ser. Nos. 08/977,845, filed on Nov. 25, 1997, 08/942,580, filed on Oct. 2, 1997, U.S. application Ser. No. 08/753,227, filed on Nov. 22, 1996, U.S. application Ser. No. 08/687,792, filed on Jul. 18, 1996, and PCT International Application, U.S. National Phase Ser. No. PCT/US94/05168, filed on May 10, 1994, now U.S. Pat. No. 5,697,909, which was a continuation-in-part of U.S. patent application Ser. No. 08/059,681, filed on May 10, 1993, which was a continuation-in-part of U.S. patent application Ser. No. 07/958,977, filed on Oct. 9, 1992 which was a continuation-in-part of U.S. patent application Ser. No. 07/817,575, filed on Jan. 7, 1992, the complete disclosures of which are incorporated herein by reference for all purposes. The present invention is also related to commonly assigned U.S. Pat. No. 5,683,366, filed Nov. 22, 1995, the complete disclosure of which is incorporated herein by reference for all purposes.

BACKGROUND OF THE INVENTION

The present invention relates generally to the field of electrosurgery, and more particularly to surgical devices and methods which employ high frequency electrical energy to treat tissue in regions of the head and neck, such as the brain and spinal cord.

Cerebrovascular diseases are those in which brain diseases occur secondary to the pathological disorder of blood vessels (usually arteries) or the blood supply. This pathological disorder has a variety of mechanisms, including vessel occlusion by thrombus or embolus, rupture or disease of the blood vessel wall and disturbances in the normal properties of blood flowing through the brain. Regardless of the mechanism, the resultant effect on the brain is either ischaemia/infarction or haemorrhagic disruption (i.e., stroke).

Medical treatment for cerebrovascular disease has included anticoagulant therapy and the use of thrombolytic agents. The effectiveness of anticoagulant agents is uncertain and the risk of recurrent embolic infarction is high. Similarly, thrombolytic agents pose a relatively high risk of intracranial hemorrhage.

Surgical treatment for vascular diseases has included a number of catheter-based approaches, such as balloon angioplasty and endartectomy. Endartectomy procedures typically involve introducing a catheter having a cup-shaped rotating cutter into the vascular system to sever and capture at least a portion of the occlusive material. Other interventional techniques includes laser ablation, mechanical abrasion, chemical dissolution, hot-tipped catheters, drill-tipped catheters and the like. While promising, these techniques have a few drawbacks. For some of these techniques (e.g., balloon angioplasty), it is often difficult to advance the distal end of the catheter through the stenosed region in extremely narrow vessels, such as those encountered in the brain. Under these circumstances, it may be necessary to at least partially recanalize the occlusion before the catheter procedure can begin. Other techniques (e.g., hot-tipped or drill-tipped catheters) rely on very aggressive treatment of the occlusive material to open up a passage. Such aggressive techniques can expose the blood vessel wall to significant injury, for example, vessel perforation.

The present invention is also concerned with the removal of benign or malignant tumors in the head and neck, such as neuromas, meninges, neuroepithelial tumors, lymphomas, metastatic tumors and the like. Unfortunately, conventional techniques for removing such tumors, such as electrosurgery, powered instruments and lasers, are not very precise, and they often cause damage or necrosis to surrounding or underlying body structures, which can be extremely problematic in the brain. Moreover, it is often difficult to differentiate between the target tumor tissue, and other neighboring body structures, such as cartilage, bone or nerves. In particular, many tumors in the head and neck are located closely adjacent to nerves. Nerve injury can lead to muscle paralysis, pain, exaggerated reflexes, loss of bladder control, impaired cough reflexes, spasticity and other conditions. Thus, the surgeon utilizing conventional devices must be extremely careful to avoid damaging the nerves that extend through the target site.

Further, conventional techniques for removing such tumors generally result in the production of smoke in the surgical setting, termed an electrosurgical or laser plume, which can spread intact, viable bacterial or viral particles from the tumor or lesion to the surgical team or to other portions of the patient's body. Numerous studies have confirmed that viable cells, such as papillomavirus, HIV, cancer cells, and the like, are spread to other portions of the patient's body during these tumor removal procedures. In conventional RF devices, for example, a high frequency voltage is applied between two electrodes in either a monopolar or bipolar mode to create intense heat at the target site that causes the inner cellular fluid to explode, producing a cutting effect along the path of the device. This cutting effect generally results in the production of smoke, or an electrosurgical plume, which can spread bacterial or viral particles from the tissue to the surgical team or to other portions of the patient's body. In addition, the tissue is parted along the pathway of evaporated cellular fluid, inducing undesirable collateral tissue damage in regions surrounding the target tissue site.

SUMMARY OF THE INVENTION

The present invention provides systems, apparatus and methods for selectively applying electrical energy to structures in the brain and spinal cord. The systems and methods of the present invention are particularly useful for treating cerebrovascular diseases, such as vessel occlusion, or for the volumetric removal or ablation of intracranial tumors or Arteriovenous Malformations (AVM).

The method of the present invention comprises positioning an electrosurgical probe or catheter adjacent the target site so that one or more electrode terminal(s) and one or more return electrode(s) are brought into at least partial contact or close proximity with a body structure within the patient's head or neck, such as tumor tissue or an occlusion within a blood vessel. High frequency voltage is then applied between the electrode terminal(s) and return electrode(s) to volumetrically remove or ablate at least a portion of the body structure in situ. The present invention is particularly useful for volumetrically removing atheromatous or thrombotic occlusions in blood vessels, or benign or malignant tumors in the brain.

In a specific aspect of the invention, a method is provided for volumetrically removing occlusive media from blood vessels within the brain to treat cerebrovascular diseases. In this method, a catheter is advanced intraluminally to the target site within the vessel such that one or more electrode terminal(s) are positioned adjacent to or in contact with the vessel occlusion. In a preferred embodiment, an electrically conducting fluid is directed to the target site so that the fluid is located between the electrode terminal(s) and one or more return electrode(s) positioned proximal to the electrode terminal(s) to provide a current flow path from the electrode terminal(s) to the return electrode(s). High frequency voltage is applied between the electrode terminal(s) and the return electrode(s) to volumetrically remove or ablate at least a portion of the occlusive media.

In another aspect of the invention, a method is provided for removing or ablating intracranial tumors or AVMs from a patient's brain. An electrosurgical instrument (i.e., catheter or probe) is guided to the target site in a conventional manner, i.e., percutaneously, transluminally or using other minimally invasive or open surgery techniques. The target site in the brain may be charted with a variety of imaging techniques, such as computerized tomography (CT) scanning, magnetic resonance imaging (MRI), ultrasound, angiography, radionucleotide imaging, electroencephalography (EEG) and the like. In conjunction with one of these imaging procedures, typically CT or MRI, the present invention may also use compatible stereotactic systems for guiding the instrument to the target location. Once the distal end of the instrument is positioned adjacent the target site, an electrically conducting fluid is directed thereto to provide the current flow path between the electrode terminal(s) and the return electrode. The high frequency voltage is sufficient to volumetrically remove the tumor while minimizing the collateral damage to surrounding tissue and/or nerves within the brain. In specific embodiments, the high frequency voltage is sufficient to effect the dissociation or disintegration of organic molecules into non-viable atoms and molecules. Specifically, the present invention converts the solid tissue cells into non-condensable gases that are no longer intact or viable, and thus, not capable of seeding cancerous cells to other portions of the body structure. A more complete description of this phenomena can be found in commonly assigned, co-pending U.S. application Ser. No. 09/109,219, previously incorporated herein by reference.

In preferred embodiments, the material, e.g., tumor or occlusive media, is removed by molecular dissociation or disintegration processes. In these embodiments, the high frequency voltage applied to the electrode terminal(s) is sufficient to vaporize an electrically conductive fluid (e.g., gel or saline) between the electrode terminal(s) and the tissue. Within the vaporized fluid, an ionized plasma is formed and charged particles (e.g., electrons) are accelerated towards the tissue to cause the molecular breakdown or disintegration of several cell layers of the tissue. This molecular dissociation is accompanied by the volumetric removal of the tissue. The short range of the accelerated charged particles within the plasma layer confines the molecular dissociation process to the surface layer to minimize damage and necrosis to the underlying tissue. This process can be precisely controlled to effect the volumetric removal of tissue as thin as 10 to 150 microns with minimal heating of, or damage to, surrounding or underlying tissue structures. A more complete description of this phenomena is described in commonly assigned U.S. Pat. No. 5,683,366.

In yet another aspect of the invention, a method is provided for treating aneurysms within a patient's brain. In this method, a flowable substance, such as collagen, is delivered to the site of an aneurysm, and an electrosurgical instrument is positioned at the target site in one of the manners described above. A high frequency voltage difference is applied between one or more electrode terminal(s) and one or more return electrode(s) at or near the target site. The high frequency voltage difference is sufficient to harden the substance such that the hardened substance covers the weak region of the blood vessel wall causing the aneurysm. The hardened substance may also provide a base onto which epithelial cells of the blood vessel may grow, providing a new and stronger blood vessel wall. In preferred embodiments, an electrically conductive fluid is delivered to the target site to provide a conductive path between the electrode terminal(s) and the return electrode(s).

Apparatus according to the present invention generally include an electrosurgical instrument having a shaft with proximal and distal ends, one or more electrode terminal(s) at the distal end and one or more connectors coupling the electrode terminal(s) to a source of high frequency electrical energy. In some embodiments, the instrument will comprise a catheter designed for percutaneous and/or transluminal delivery to the brain. In other embodiments, the instrument will comprise a more rigid probe designed for percutaneous or direct delivery to the brain in either open procedures or port access type procedures. In both embodiments, the apparatus will include a high frequency power supply for applying a high frequency voltage to the electrode terminal (s). The voltage is sufficient to volumetrically remove at least a portion of the tissue or occlusive mass in situ while minimizing damage to the healthy tissue.

The apparatus will preferably further include a fluid delivery element for delivering electrically conducting fluid to the electrode terminal(s) and the target site. The fluid delivery element may be located on the instrument, e.g., a fluid lumen or tube, or it may be part of a separate instrument. Alternatively, an electrically conducting gel or spray, such as a saline electrolyte or other conductive gel, may be applied to the target site. In this embodiment, the apparatus may not have a fluid delivery element. In both embodiments, the electrically conducting fluid will preferably generate a current flow path between the electrode terminal(s) and one or more return electrode(s). In an exemplary embodiment, the return electrode is located on the instrument and spaced a sufficient distance from the electrode terminal(s) to substantially avoid or minimize current shorting therebetween and to shield the return electrode from tissue at the target site.

In a specific configuration, the electrosurgical instrument will include an electrically insulating electrode support member, preferably an inorganic support material (e.g., ceramic, glass, glass/ceramic, etc.) having a tissue treatment surface at the distal end of the instrument shaft. One or more electrode terminal(s) are coupled to, or integral with, the electrode support member such that the electrode terminal(s) are spaced from the return electrode. In one embodiment, the instrument includes an electrode array having a plurality of electrically isolated electrode terminals embedded into the electrode support member such that the electrode terminals extend about 0.0 mm to about 10 mm distally from the tissue treatment surface of the electrode support member. In this embodiment, the probe will further include one or more lumens for delivering electrically conductive fluid and/or aspirating the target site to one or more openings around the tissue treatment surface of the electrode support member. In an exemplary embodiment, the lumen will extend through a fluid tube exterior to the probe shaft that ends proximal to the return electrode.

DESCRIPTION OF SPECIFIC EMBODIMENTS

Figure 1:
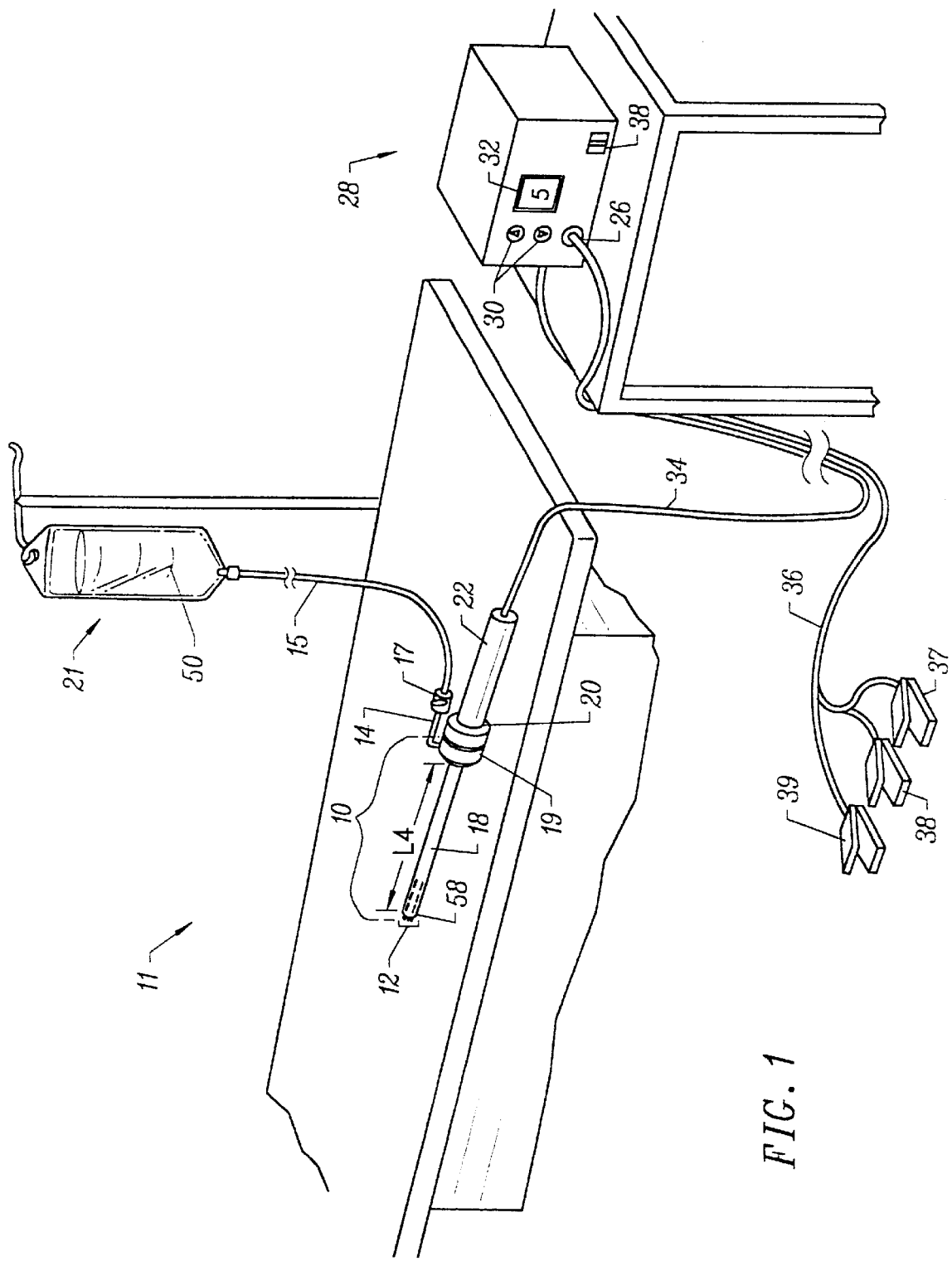
FIG. 1 is a perspective view of an electrosurgical system incorporating a power supply and an electrosurgical probe for tissue ablation, resection, incision, contraction and for vessel hemostasis according to the present invention.

The present invention provides systems and methods for selectively applying electrical energy to a target location within or on a patient's body, particularly including tissue in the brain and spinal cord. The methods and apparatus of the present invention are also useful for removing atheromatous material which partially or fully occludes a body lumen, such as a blood vessel within the brain. In fact, the methods and apparatus disclosed herein may be used in a wide variety of procedures, including open procedures, intravascular procedures, urology, laparascopy, arthroscopy, thoracoscopy or other cardiac procedures, dermatology, orthopedics, gynecology, otorhinolaryngology, spinal and other neurologic procedures, oncology and the like. For convenience, the remaining disclosure will be directed specifically to the removal of undesirable material from the brain, In the present invention, high frequency (RF) electrical energy is applied to one or more electrode terminals in the presence of electrically conductive fluid to remove and/or modify the structure of tissue structures. Depending on the specific procedure, the present invention may be used to: (1) volumetrically remove tissue, tumors, bone, occlusive media, cartilage or the like (i.e., ablate or effect molecular dissociation of the body structure); (2) cut or resect body structures; (3) shrink or contract collagen connective tissue; and/or (4) coagulate severed blood vessels.

The techniques of the present invention will typically be performed in conjunction with instrument guiding technology for guiding the surgical instrument to the target site within the head and neck, e.g., the brain. In this regard, the present invention may use a variety of imaging techniques, such as computerized tomography (CT) scanning, magnetic resonance imaging (MRI), ultrasound, angiography, radionucleotide imaging, electroencephalography (EEG) and the like. In conjunction with one of these imaging procedures, typically CT or MRI, the present invention may also use compatible stereotactic systems for guiding the instrument to the target location. In standard stereotactic systems, a frame, e.g., a Leksell, Todd-Wells or Guiot frame, fixes the patient's head to the image. These frames, combined with radiological landmarks and a brain atlas, provide anatomical localization to within +−1 mm. Alternatively, imaged guided frameless stereotactic systems that utilize modern imaging, elaborate computer software and a locating device, may be employed with the present invention.

The techniques of the present invention may be performed percutaneously by introducing an electrosurgical instrument into the patient's vasculature and advancing the instrument transluminally to a target site. These procedures may also be performed through other ninimally invasive methods, such as introducing a surgical probe and endoscope through a small opening, e.g., a burr hole, in the patient's cranium, or through natural openings in the patient's head, such as transoral or transphenoidal procedures. The present invention may further be performed using traditional open surgery techniques.

In one aspect of the invention, the tissue or occlusive material is volumetrically removed or ablated. In this procedure, a high frequency voltage difference is applied between one or more electrode terminal(s) and one or more return electrode(s) to develop high electric field intensities in the vicinity of the target tissue. The high electric field intensities adjacent the electrode terminal(s) lead to electric field induced molecular breakdown of target tissue through molecular dissociation (rather than thermal evaporation or carbonization). Applicant believes that the tissue structure is volumetrically removed through molecular disintegration of larger organic molecules into smaller molecules and/or atoms, such as hydrogen, oxygen, oxides of carbon, hydrocarbons and nitrogen compounds. This molecular disintegration completely removes the tissue structure, as opposed to dehydrating the tissue material by the removal of liquid within the cells of the tissue, as is typically the case with electrosurgical desiccation and vaporization.

The high electric field intensities may be generated by applying a high frequency voltage that is sufficient to vaporize an electrically conducting fluid over at least a portion of the electrode terminal(s) in the region between the distal tip of the electrode terminal(s) and the target tissue. The electrically conductive fluid may be a liquid, such as isotonic saline or blood, delivered to the target site, or a viscous fluid, such as a gel, applied to the target site. Since the vapor layer or vaporized region has a relatively high electrical impedance, it increases the voltage differential between the electrode terminal tip and the tissue and causes ionization within the vapor layer due to the presence of an ionizable species (e.g., sodium when isotonic saline is the electrically conducting fluid). This ionization, under optimal conditions, induces the discharge of energetic electrons and photons from the vapor layer and to the surface of the target tissue. This energy may be in the form of energetic photons (e.g., ultraviolet radiation), energetic particles (e.g., electrons) or a combination thereof. A more detailed description of this phenomena, termed Coblation™ can be found in commonly assigned U.S. Pat. No. 5,683,366 the complete disclosure of which is incorporated herein by reference.

In some procedures, e.g., treatment of aneurysms, it is desired to apply sufficient thermal energy to a hardenable substance, such as collagen, to harden (e.g., shrink or contract) the substance at the target site. In these procedures, the RF energy heats the fluid substance directly by virtue of the electrical current flow therethrough, and/or indirectly through the exposure of the fluid substance to fluid heated by RF energy, to elevate the substance temperature from normal body temperatures (e.g., 37° C.) to temperatures in the range of 45° C. to 90° C., preferably in the range from about 60° C. to 70° C. Thermal shrinkage of collagen fibers, for example, occurs within a small temperature range which, for mammalian collagen is in the range from 60° C. to 70° C. (Deak, G., et al., "The Thermal Shrinkage Process of Collagen Fibres as Revealed by Polarization Optical Analysis of Topooptical Staining Reactions," Acta Morphologica Acad. Sci. of Hungary, Vol. 15(2), pp 195–208, 1967). Collagen fibers typically undergo thermal shrinkage in the range of 60° C. to about 70° C. Previously reported research has attributed thermal shrinkage of collagen to the cleaving of the internal stabilizing cross-linkages within the collagen matrix (Deak, ibid). It has also been reported that when the collagen temperature is increased above 70° C., the collagen matrix begins to relax again and the shrinkage effect is reversed resulting in no net shrinkage (Allain, J. C., et al., "Isometric Tensions Developed During the Hydrothermal Swelling of Rat Skin," Connective Tissue Research, Vol. 7, pp 127–133, 1980). A more detailed description of collagen shrinkage can be found in U.S. patent application Ser. No. 08/942,580, filed Oct. 2, 1997, entitled "SYSTEMS AND METHODS FOR ELECTROSURGICAL TISSUE CONTRACTION", previously incorporated herein by reference.

In other embodiments, the present invention applies high frequency (RF) electrical energy in an electrically conducting fluid environment to remove (i.e., resect, cut or ablate) a tissue structure and to seal transected vessels within the region of the target tissue. The present invention is particularly useful for sealing larger arterial vessels, e.g., on the order of 1 mm or greater. In some embodiments, a high frequency power supply is provided having an ablation mode, wherein a first voltage is applied to an electrode terminal sufficient to effect molecular dissociation or disintegration of the tissue, and a coagulation mode, wherein a second, lower voltage is applied to an electrode terminal (either the same or a different electrode) sufficient to achieve hemostasis of severed vessels within the tissue. In other embodiments, an electrosurgical instrument is provided having one or more coagulation electrode(s) configured for sealing a severed vessel, such as an arterial vessel, and one or more electrode terminals configured for either contracting the collagen fibers within the tissue or removing (ablating) the tissue, e.g., by applying sufficient energy to the tissue to effect molecular dissociation. In the latter embodiments, the coagulation electrode(s) may be configured such that a single voltage can be applied to coagulate with the coagulation electrode(s), and to ablate with the electrode terminal (s). In other embodiments, the power supply is combined with the coagulation instrument such that the coagulation electrode is used when the power supply is in the coagulation mode (low voltage), and the electrode terminal(s) are used when the power supply is in the ablation mode (higher voltage).

In one method of the present invention, one or more electrode terminals are brought into close proximity to tissue at a target site, and the power supply is activated in the ablation mode such that sufficient voltage is applied between the electrode terminals and the return electrode to volumetrically remove the tissue through molecular dissociation, as described below. During this process, vessels within the tissue will be severed. Smaller vessels will be automatically sealed with the system and method of the present invention. Larger vessels, and those with a higher flow rate, such as arterial vessels, may not be automatically sealed in the ablation mode. In these cases, the severed vessels may be sealed by activating a control (e.g., a foot pedal) to reduce the voltage of the power supply into the coagulation mode. In this mode, the electrode terminals may be pressed against the severed vessel to provide sealing and/or coagulation of the vessel.

Alternatively, a coagulation electrode located on the same or a different instrument may be pressed against the severed vessel. Once the vessel is adequately sealed, the surgeon activates a control (e.g., another foot pedal) to increase the voltage of the power supply back into the ablation mode.

The present invention is also useful for removing or ablating tissue around nerves, such as spinal, or cranial nerves, e.g., optic nerve, facial nerves, vestibulocochlear nerves and the like. This is particularly advantageous when removing certain brain tumors that are located close to cranial nerves. One of the significant drawbacks with the prior art microdebriders and lasers is that these devices do not differentiate between the target tissue and the surrounding nerves or bone. Therefore, the surgeon must be extremely careful during these procedures to avoid damage to the bone or nerves within and around the nasal cavity. In the present invention, the Coblation™ process for removing tissue results in extremely small depths of collateral tissue damage as discussed above. This allows the surgeon to remove tissue close to a nerve without causing collateral damage to the nerve fibers.

In addition to the generally precise nature of the novel mechanisms of the present invention, applicant has discovered an additional method of ensuring that adjacent nerves are not damaged during tissue removal. According to the present invention, systems and methods are provided for distinguishing between the fatty tissue immediately surrounding nerve fibers and the normal tissue that is to be removed during the procedure. Nerves usually comprise a connective tissue sheath, or epineurium, enclosing the bundles of nerve fibers, each bundle being surrounded by its own sheath of connective tissue (the perineurium) to protect these nerve fibers. The outer protective tissue sheath or epineurium typically comprises a fatty tissue (e.g., adipose tissue) having substantially different electrical properties than the normal target tissue, such as the turbinates, polyps, mucus tissue or the like, that are, for example, removed from the nose during sinus procedures. The system of the present invention measures the electrical properties of the tissue at the tip of the probe with one or more electrode terminal(s). These electrical properties may include electrical conductivity at one, several or a range of frequencies (e.g., in the range from 1 kHz to 100 MHz), dielectric constant, capacitance or combinations of these. In this embodiment, an audible signal may be produced when the sensing electrode (s) at the tip of the probe detects the fatty tissue surrounding a nerve, or direct feedback control can be provided to only supply power to the electrode terminal(s) either individually or to the complete array of electrodes, if and when the tissue encountered at the tip or working end of the probe is normal tissue based on the measured electrical properties.

In one embodiment, the current limiting elements (discussed in detail above) are configured such that the electrode terminals will shut down or turn off when the electrical impedance reaches a threshold level. When this threshold level is set to the impedance of the fatty tissue surrounding nerves, the electrode terminals will shut off whenever they come in contact with, or in close proximity to, nerves. Meanwhile, the other electrode terminals, which are in contact with or in close proximity to nasal tissue, will continue to conduct electric current to the return electrode. This selective ablation or removal of lower impedance tissue in combination with the Coblation™ mechanism of the present invention allows the surgeon to precisely remove tissue around nerves or bone. Applicant has found that the present invention is capable of volumetrically removing tissue closely adjacent to nerves without impairment the function of the nerves, and without significantly damaging the tissue of the epineurium. One of the significant drawbacks with the prior art microdebriders, RF devices and lasers is that these devices do not differentiate between the target tissue and the surrounding nerves or bone. Therefore, the surgeon must be extremely careful during these procedures to avoid damage to the bone or nerves within and around the nasal cavity. In the present invention, the Coblation™ process for removing tissue results in extremely small depths of collateral tissue damage as discussed above. This allows the surgeon to remove tissue close to a nerve without causing collateral damage to the nerve fibers.

In addition to the above, applicant has discovered that the Coblation™ mechanism of the present invention can be manipulated to ablate or remove certain tissue structures, while having little effect on other tissue structures. As discussed above, the present invention uses a technique of vaporizing electrically conductive fluid to form a plasma layer or pocket around the electrode terminal(s), and then inducing the discharge of energy from this plasma or vapor layer to break the molecular bonds of the tissue structure. Based on initial experiments, applicants believe that the free electrons within the ionized vapor layer are accelerated in the high electric fields near the electrode tip(s). When the density of the vapor layer (or within a bubble formed in the electrically conducting liquid) becomes sufficiently low (i;e., less than approximately $10^{20}$ atoms/cm$^3$ for aqueous solutions), the electron mean free path increases to enable subsequently injected electrons to cause impact ionization within these regions of low density (i.e., vapor layers or bubbles). Energy evolved by the energetic electrons (e.g., 4 to 5 eV) can subsequently bombard a molecule and break its bonds, dissociating a molecule into free radicals, which then combine into final gaseous or liquid species.

The energy evolved by the energetic electrons may be varied by adjusting a variety of factors, such as: the number of electrode terminals; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Accordingly, these factors can be manipulated to control the energy level of the excited electrons. Since different tissue structures have different molecular bonds, the present invention can be configured to break the molecular bonds of certain tissue, while having too low an energy to break the molecular bonds of other tissue. For example, fatty tissue, (e.g., adipose) tissue has double bonds that require a substantially higher energy level than 4 to 5 eV to break. Accordingly, the present invention in its current configuration generally does not ablate or remove such fatty tissue. Of course, factors may be changed such that these double bonds can also be broken in a similar fashion as the single bonds (e.g., increasing voltage or changing the electrode configuration to increase the current density at the electrode tips). A more complete description of this phenomena can be found in co-pending U.S. patent application Ser. No. 09/032,375, filed Feb. 27, 1998, the complete disclosure of which is incorporated herein by reference.

The present invention also provides systems, apparatus and methods for selectively removing brain tumors or other undesirable body structures while minimizing the spread of viable cells from the tumor. Conventional techniques for removing such tumors generally result in the production of smoke in the surgical setting, termed an electrosurgical or laser plume, which can spread intact, viable bacterial or viral particles from the tumor or lesion to the surgical team or to other portions of the patient's body. This potential spread of viable cells or particles has resulted in increased concerns over the proliferation of certain debilitating and fatal diseases, such as hepatitis, herpes, HIV and papillomavirus. In the present invention, high frequency voltage is applied between the electrode terminal(s) and one or more return electrode(s) to volumetrically remove at least a portion of the tissue cells in the tumor through the dissociation or disintegration of organic molecules into non-viable atoms and molecules. Specifically, the present invention converts the solid tissue cells into non-condensable gases that are no longer intact or viable, and thus, not capable of spreading viable tumor particles to other portions of the patient's brain or to the surgical staff. The high frequency voltage is preferably selected to effect controlled removal of these tissue cells while minimizing substantial tissue necrosis to surrounding or underlying tissue. A more complete description of this phenomena can be found in co-pending U.S. patent application Ser. No. 09/109,219, filed Jun. 30, 1998, the complete disclosure of which is incorporated herein by reference The electrosurgical instrument will comprise a shaft having a proximal end and a distal end which supports one or more electrode terminal(s). The shaft may assume a wide variety of configurations, with the primary purpose being to mechanically support one or more electrode terminal(s) and permit the treating physician to manipulate the electrode(s) from a proximal end of the shaft. Usually, an electrosurgical probe shaft will be a narrow-diameter rod or tube, more usually having dimensions which permit it to be introduced through a burr hole, flap of bone cut or the like in the patient's cranium, or through a conventional transoral or transphenoidal route. Thus, the probe shaft will typically have a length of at least 5 cm for open procedures and at least 10 cm, more typically being 20 cm, or longer for endoscopic procedures. The probe shaft will typically have a diameter of at least 1 mm and frequently in the range from 1 to 10 mm.

The electrosurgical instrument may be delivered percutaneously and/or endoluminally to the brain by insertion through a conventional or specialized guide catheter, or the invention may include a catheter having an active electrode or electrode array integral with its distal end. The catheter shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode or electrode array. The catheter haft will usually include a plurality of wires or other conductive elements running axially therethrough to permit connection of the electrode or electrode array and the return electrode to a connector at the proximal end of the catheter shaft. The catheter shaft may include a guide wire for guiding the catheter to the target site, or the catheter may comprise a steerable guide catheter. The catheter may also include a substantially rigid distal end portion to increase the torque control of the distal end portion as the catheter is advanced further into the patient's body. Specific shaft designs will be described in detail in connection with the figures hereinafter.

The electrode terminal(s) are preferably supported within or by an inorganic insulating support positioned near the distal end of the instrument shaft. The return electrode may be located on the instrument shaft, on another instrument or on the external surface of the patient (i.e., a dispersive pad). The close proximity of nerves and other sensitive tissue in the brain, however, makes a bipolar design more preferable because this minimizes the current flow through brain tissue and surrounding nerves. Accordingly, the return electrode is preferably either integrated with the catheter body, or another instrument located in close proximity to the distal end of the catheter body. The proximal end of the catheter will include the appropriate electrical connections for coupling the return electrode(s) and the electrode terminal(s) to a high frequency power supply, such as an electrosurgical generator.

The current flow path between the electrode terminals and the return electrode(s) may be generated by submerging the tissue site in an electrical conducting fluid (e.g., within a viscous fluid, such as an electrically conductive gel) or by directing an electrically conducting fluid along a fluid path to the target site (i.e., a liquid, such as isotonic saline, or a gas, such as argon). The conductive gel may also be delivered to the target site to achieve a slower more controlled delivery rate of conductive fluid. In addition, the viscous nature of the gel may allow the surgeon to more easily contain the gel around the target site (e.g., rather than attempting to contain isotonic saline). A more complete description of an exemplary method of directing electrically conducting fluid between the active and return electrodes is described in U.S. Pat. No. 5,697,281, previously incorporated herein by reference. Alternatively, the body's natural conductive fluids, such as blood, may be sufficient to establish a conductive path between the return electrode(s) and the electrode terminal(s), and to provide the conditions for establishing a vapor layer, as described above. However, conductive fluid that is introduced into the patient is generally preferred over blood because blood will tend to coagulate at certain temperatures. Advantageously, a liquid electrically conductive fluid (e.g., isotonic saline) may be used to concurrently "bathe" the target tissue surface to provide an additional means for removing any tissue, and to cool the region of the target tissue ablated in the previous moment.

The power supply may include a fluid interlock for interrupting power to the electrode terminal(s) when there is insufficient conductive fluid around the electrode terminal (s). This ensures that the instrument will not be activated when conductive fluid is not present, minimizing the tissue damage that may otherwise occur. A more complete description of such a fluid interlock can be found in commonly assigned, co-pending U.S. application Ser. No. 09/058,336, filed Apr. 10, 1998, the complete disclosure of which is incorporated herein by reference.

In some procedures, it may also be necessary to retrieve or aspirate the electrically conductive fluid and/or the non-condensable gaseous products of ablation. For example, in procedures in and around the brain and its surrounding blood vessels, it may be desirable to aspirate the fluid so that it does not flow downstream. In addition, it may be desirable to aspirate small pieces of tissue or other body structures that are not completely disintegrated by the high frequency energy, or other fluids at the target site, such as blood, mucus, the gaseous products of ablation, etc. Accordingly, the system of the present invention may include one or more suction lumen(s) in the instrument, or on another instrument, coupled to a suitable vacuum source for aspirating fluids from the target site. In addition, the invention may include one or more aspiration electrode(s) coupled to the distal end of the suction lumen for ablating, or at least reducing the volume of, non-ablated tissue fragments that are aspirated into the lumen. The aspiration electrode(s) function mainly to inhibit clogging of the lumen that may otherwise occur as larger tissue fragments are drawn therein. The aspiration electrode(s) may be different from the ablation electrode terminal(s), or the same electrode(s) may serve both functions. A more complete description of instruments incorporating aspiration electrode(s) can be found in commonly assigned, co-pending patent application entitled "Systems And Methods For Tissue Resection, Ablation And Aspiration", filed Jan. 21, 1998, the complete disclosure of which is incorporated herein by reference.

As an alternative or in addition to suction, it may be desirable to contain the excess electrically conductive fluid, tissue fragments and/or gaseous products of ablation at or near the target site with a containment apparatus, such as a basket, retractable sheath or the like. This embodiment has the advantage of ensuring that the conductive fluid, tissue fragments or ablation products do not flow through the patient's vasculature or into other portions of the body. In addition, it may be desirable to limit the amount of suction to limit the undesirable effect suction may have on hemostasis of severed blood vessels.

The present invention may use a single active electrode terminal or an array of electrode terminals spaced around the distal surface of a catheter or probe. In the latter embodiment, the electrode array usually includes a plurality of independently current-limited and/or power-controlled electrode terminals to apply electrical energy selectively to the target tissue while limiting the unwanted application of electrical energy to the surrounding tissue and environment resulting from power dissipation into surrounding electrically conductive fluids, such as blood, normal saline, and the like. The electrode terminals may be independently current-limited by isolating the terminals from each other and connecting each terminal to a separate power source that is isolated from the other electrode terminals. Alternatively, the electrode terminals may be connected to each other at either the proximal or distal ends of the catheter to form a single wire that couples to a power source.

In one configuration, each individual electrode terminal in the electrode array is electrically insulated from all other electrode terminals in the array within said instrument and is connected to a power source which is isolated from each of the other electrode terminals in the array or to circuitry which limits or interrupts current flow to the electrode terminal when low resistivity material (e.g., blood, electrically conductive saline irrigant or electrically conductive gel) causes a lower impedance path between the return electrode and the individual electrode terminal. The isolated power sources for each individual electrode terminal may be separate power supply circuits having internal impedance characteristics which limit power to the associated electrode terminal when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the electrode terminals through independently actuatable switches, or by independent current limiting elements, such as inductors, capacitors, resistors and/or combinations thereof. The current limiting elements may be provided in the instrument, connectors, cable, controller or along the conductive path from the controller to the distal tip of the instrument. Alternatively, the resistance and/or capacitance may occur on the surface of the active electrode terminal(s) due to oxide layers which form selected electrode terminals (e.g., titanium or a resistive coating on the surface of metal, such as platinum).

The tip region of the instrument may comprise many independent electrode terminals designed to deliver electrical energy in the vicinity of the tip. The selective application of electrical energy to the conductive fluid is achieved by connecting each individual electrode terminal and the return electrode to a power source having independently controlled or current limited channels. The return electrode(s) may comprise a single tubular member of conductive material proximal to the electrode array at the tip which also serves as a conduit for the supply of the electrically conducting fluid between the active and return electrodes. Alternatively, the instrument may comprise an array of return electrodes at the distal tip of the instrument (together with the active electrodes) to maintain the electric current at the tip. The application of high frequency voltage between the return electrode(s) and the electrode array results in the generation of high electric field intensities at the distal tips of the electrode terminals with conduction of high frequency current from each individual electrode terminal to the return electrode. The current flow from each individual electrode terminal to the return electrode(s) is controlled by either active or passive means, or a combination thereof, to deliver electrical energy to the surrounding conductive fluid while minimizing energy delivery to surrounding (non-target) tissue.

The application of a high frequency voltage between the return electrode(s) and the electrode terminal(s) for appropriate time intervals effects cutting, removing, ablating, shaping, contracting or otherwise modifying the target tissue. The tissue volume over which energy is dissipated (i.e., a high current density exists) may be precisely controlled, for example, by the use of a multiplicity of small electrode terminals whose effective diameters or principal dimensions range from about 10 mm to 0.01 mm, preferably from about 2 mm to 0.05 mm, and more preferably from about 1 mm to 0.1 mm. Electrode areas for both circular and non-circular terminals will have a contact area (per electrode terminal) below 50 mm$^2$ for electrode arrays and as large as 75 mm$^2$ for single electrode embodiments, preferably being in the range from 0.0001 mm$^2$ to 1 mm$^2$, and more preferably from 0.005 mm$^2$ to 0.5$^2$. The circumscribed area of the electrode array is in the range from 0.25 mm$^2$ to 75 mm$^2$, preferably from 0.5 mm$^2$ to 40 mm$^2$, and will usually include at least one electrode terminal and in some embodiments includes at least two isolated electrode terminals, often at least five electrode terminals, often greater than 10 electrode terminals and even 50 or more electrode terminals, disposed over the distal contact surfaces on the shaft. The use of small diameter electrode terminals increases the electric field intensity and reduces the extent or depth of tissue heating as a consequence of the divergence of current flux lines which emanate from the exposed surface of each electrode terminal.

The area of the tissue treatment surface can vary widely, and the tissue treatment surface can assume a variety of geometries, with particular areas and geometries being selected for specific applications. The active electrode surface(s) can have area(s) in the range from 0.25 mm$^2$ to 75 mm$^2$, usually being from about 0.5 mm$^2$ to 40 mm$^2$. The geometries can be planar, concave, convex, hemispherical, conical, linear "in-line" array or virtually any other regular or irregular shape. Most commonly, the active electrode(s) or electrode terminal(s) will be formed at the distal tip of the electrosurgical instrument shaft, frequently being planar, disk-shaped, or hemispherical surfaces for use in reshaping procedures or being linear arrays for use in cutting. Alternatively or additionally, the active electrode(s) may be formed on lateral surfaces of the electrosurgical instrument shaft (e.g., in the manner of a spatula), facilitating access to certain body structures in endoscopic procedures.

In some embodiments, the electrode support and the fluid outlet may be recessed from an outer surface of the instrument or handpiece to confine the electrically conductive fluid to the region immediately surrounding the electrode support. In addition, the shaft may be shaped so as to form a cavity around the electrode support and the fluid outlet. This helps to assure that the electrically conductive fluid will remain in contact with the electrode terminal(s) and the return electrode(s) to maintain the conductive path therebetween. In addition, this will help to maintain a vapor layer and subsequent plasma layer between the electrode terminal(s) and the tissue at the treatment site throughout the procedure, which reduces the thermal damage that might otherwise occur if the vapor layer were extinguished due to a lack of conductive fluid. Provision of the electrically conductive fluid around the target site also helps to maintain the tissue temperature at desired levels.

The electrically conducting fluid should have a threshold conductivity to provide a suitable conductive path between the return electrode and the electrode terminal(s). The electrical conductivity of the fluid (in units of milliSiemans per centimeter or mS/cm) will usually be greater than 0.2 mS/cm, preferably will be greater than 2 mS/cm and more preferably greater than 10 mS/cm. In an exemplary embodiment, the electrically conductive fluid is isotonic saline, which has a conductivity of about 17 mS/cm.

The voltage difference applied between the return electrode(s) and the electrode terminal(s) will be at high or radio frequency, typically between about 5 kHz and 20 MHz, usually being between about 30 kHz and 2.5 MHz, preferably being between about 50 kHz and 500 kHz, more preferably less than 350 kHz, and most preferably between about 100 kHz and 200 kHz. The RMS (root mean square) voltage applied will usually be in the range from about 5 volts to 1000 volts, preferably being in the range from about 10 volts to 500 volts depending on the electrode terminal size, the operating frequency and the operation mode of the particular procedure or desired effect on the tissue (i.e., contraction, coagulation, cutting or ablation). Typically, the peak-to-peak voltage for ablation or cutting will be in the range of 10 to 2000 volts and preferably in the range of 200 to 1800 volts and more preferably in the range of about 300 to 1500 volts, often in the range of about 500 to 900 volts peak to peak (again, depending on the electrode size, the operating frequency and the operation mode). Lower peak-to-peak voltages will be used for tissue coagulation or collagen contraction and will typically be in the range from 50 to 1500, preferably 100 to 1000 and more preferably 120 to 600 volts peak-to-peak.

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with e.g., lasers claiming small depths of necrosis, which are generally pulsed about 10 to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of target tissue being heated, and/or the maximum allowed temperature selected for the instrument tip. The power source allows the user to select the voltage level according to the specific requirements of a particular neurosurgery procedure, cardiac surgery, arthroscopic surgery, dermatological procedure, ophthalmic procedures, open surgery or other endoscopic surgery procedure. For cardiac procedures and potentially for neurosurgery, the power source may have an additional filter, for filtering leakage voltages at frequencies below 100 kHz, particularly voltages around 60 kHz. Alternatively, a power source having a higher operating frequency, e.g., 300 to 500 kHz may be used in certain procedures in which stray low frequency currents may be problematic. A description of one suitable power source can be found in co-pending patent applications Ser. Nos. 09/058,571 and 09/058,336, filed Apr. 10, 1998, the complete disclosure of both applications are incorporated herein by reference for all purposes.

The power source may be current limited or otherwise controlled so that undesired heating of the target tissue or surrounding (non-target) tissue does not occur. In a presently preferred embodiment of the present invention, current limiting inductors are placed in series with each independent electrode terminal, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in U.S. Pat. No. 5,697,909, the complete disclosure of which is incorporated herein by reference. Additionally, current limiting resistors may be selected. Preferably, these resistors will have a large positive temperature coefficient of resistance so that, as the current level begins to rise for any individual electrode terminal in contact with a low resistance medium (e.g., saline irrigant or blood), the resistance of the current limiting resistor increases significantly, thereby minimizing the power delivery from said electrode terminal into the low resistance medium (e.g., saline irrigant or blood).

It should be clearly understood that the invention is not limited to electrically isolated electrode terminals, or even to a plurality of electrode terminals. For example, the array of active electrode terminals may be connected to a single lead that extends through the catheter shaft to a power source of high frequency current. Alternatively, the instrument may incorporate a single electrode that extends directly through the catheter shaft or is connected to a single lead that extends to the power source. The active electrode(s) may have ball shapes (e.g., for tissue vaporization and desiccation), twizzle shapes (for vaporization and needle-like cutting), spring shapes (for rapid tissue debulking and desiccation), twisted metal shapes, annular or solid tube shapes or the like. Alternatively, the electrode(s) may comprise a plurality of filaments, rigid or flexible brush electrode(s) (for debulking a tumor, such as a fibroid, bladder tumor or a prostate adenoma), side-effect brush electrode(s) on a lateral surface of the shaft, coiled electrode(s) or the like.

In one embodiment, an electrosurgical catheter or probe comprises a single active electrode terminal that extends from an insulating member, e.g., ceramic, at the distal end of the shaft. The insulating member is preferably a tubular structure that separates the active electrode terminal from a tubular or annular return electrode positioned proximal to the insulating member and the active electrode. In another embodiment, the catheter or probe includes a single active electrode that can be rotated relative to the rest of the catheter body, or the entire catheter may be rotated related to the lead. The single active electrode can be positioned adjacent the abnormal tissue and energized and rotated as appropriate to remove this tissue.

The current flow path between the electrode terminal(s) and the return electrode(s) may be generated by submerging the tissue site in an electrical conducting fluid (e.g., within a viscous fluid, such as an electrically conductive gel) or by directing an electrically conducting fluid along a fluid path to the target site (i.e., a liquid, such as isotonic saline, or a gas, such as argon). This latter method is particularly effective in a dry environment (i.e., the tissue is not submerged in fluid) because the electrically conducting fluid provides a suitable current flow path from the electrode terminal to the return electrode.

Referring to FIG. 1, an exemplary electrosurgical system 11 for treatment of tissue in the brain and spinal cord will now be described in detail. Electrosurgical system 11 is generally useful for minimally invasive procedures within the brain, wherein a surgical instrument is introduced through a burr hole or other percutaneous penetration, or through a natural opening in the patient (e.g., transoral or transphenoidal procedures). System 11 generally comprises an electrosurgical handpiece or probe 10 connected to a power supply 28 for providing high frequency voltage to a target site and a fluid source 21 for supplying electrically conducting fluid 50 to probe 10. In addition, electrosurgical system 11 may include an endoscope (not shown) with a fiber optic head light for viewing the surgical site, if desired. The endoscope may be integral with probe 10, or it may be part of a separate instrument. The system 11 may also include a vacuum source (not shown) for coupling to a suction lumen or tube 220 (see FIG. 2) in the probe 10 for aspirating the target site.

As shown, probe 10 generally includes a proximal handle 19 and an elongate shaft 18 having an array 12 of electrode terminals 58 at its distal end. A connecting cable 34 has a connector 26 for electrically coupling the electrode terminals 58 to power supply 28. The electrode terminals 58 are electrically isolated from each other and each of the terminals 58 is connected to an active or passive control network within power supply 28 by means of a plurality of individually insulated conductors (not shown). A fluid supply tube 15 is connected to a fluid tube 14 of probe 10 for supplying electrically conductive fluid 50 to the target site. Conductive fluid 50 may be driven by gravity or with a suitable pump.

Power supply 28 has an operator controllable voltage level adjustment 30 to change the applied voltage level, which is observable at a voltage level display 32. Power supply 28 also includes first, second and third foot pedals 37, 38, 39 and a cable 36 which is removably coupled to power supply 28. The foot pedals 37, 38, 39 allow the surgeon to remotely adjust the energy level applied to electrode terminals 58. In an exemplary embodiment, first foot pedal 37 is used to place the power supply into the "ablation" mode and second foot pedal 38 places power supply 28 into the "subablation" mode (e.g., coagulation, tissue contraction or the like). The third foot pedal 39 allows the user to adjust the voltage level within the "ablation" mode. In the ablation mode, a sufficient voltage is applied to the electrode terminals to establish the requisite conditions for molecular dissociation of the tissue (i.e., vaporizing a portion of the electrically conductive fluid, ionizing charged particles within the vapor layer and accelerating these charged particles against the tissue). As discussed above, the requisite voltage level for ablation will vary depending on the number, size, shape and spacing of the electrodes, the distance in which the electrodes extend from the support member, etc. Once the surgeon places the power supply in the "ablation" mode, voltage level adjustment 30 or third foot pedal 39 may be used to adjust the voltage level to adjust the degree or aggressiveness of the ablation.

Of course, it will be recognized that the voltage and modality of the power supply may be controlled by other input devices. However, applicant has found that foot pedals are convenient methods of controlling the power supply while manipulating the probe during a surgical procedure.

In the subablation mode, the power supply 28 applies a low enough voltage to the electrode terminals to avoid vaporization of the electrically conductive fluid and subsequent molecular dissociation of the tissue. The surgeon may automatically toggle the power supply between the ablation and subablation modes by alternatively stepping on foot pedals 37, 38, respectively. This allows, for example, the surgeon to quickly move between coagulation and ablation in situ, without having to remove his/her concentration from the surgical field or without having to request an assistant to switch the power supply. By way of example, as the surgeon is sculpting soft tissue in the ablation mode, the probe typically will simultaneously seal and/or coagulation small severed vessels within the tissue. However, larger vessels, or vessels with high fluid pressures (e.g., arterial vessels) may not be sealed in the ablation mode. Accordingly, the surgeon can simply step on foot pedal 38, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by stepping on foot pedal 37. A specific design of a suitable power supply for use with the present invention can be found in co-pending patent applications Ser. Nos. 09/058,571 and 09/058,336, filed Apr. 10, 1998, previously incorporated herein by reference.

Figure 2:
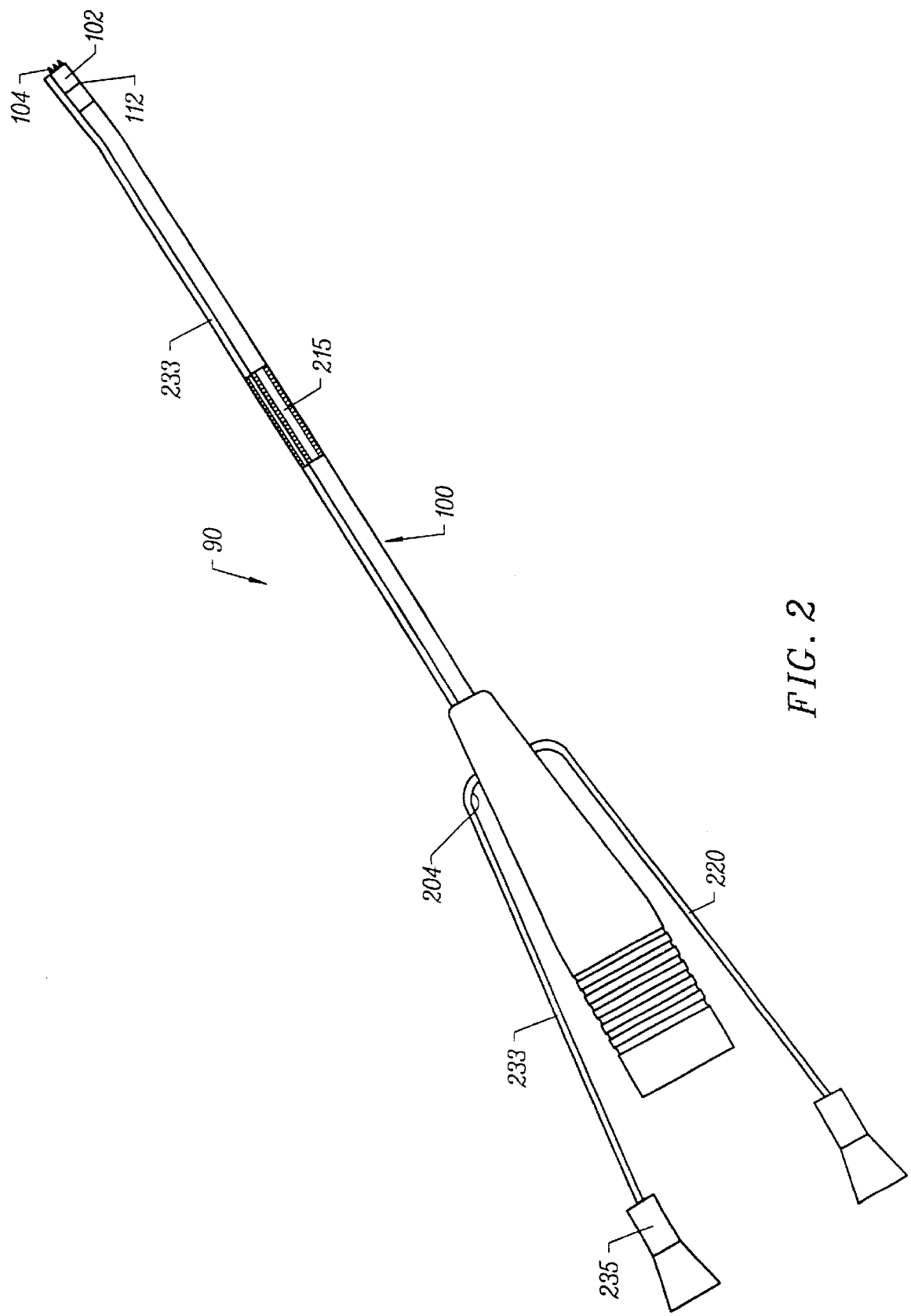
FIG. 2 is a side view of an electrosurgical probe according to the present invention.

FIGS. 2–5 illustrate an exemplary electrosurgical probe 90 constructed according to the principles of the present invention. As shown in FIG. 2, probe 90 generally includes an elongated shaft 100 which may be flexible or rigid, a handle 204 coupled to the proximal end of shaft 100 and an electrode support member 102 coupled to the distal end of shaft 100. Shaft 100 preferably comprises a plastic material that is easily molded into the shape shown in FIG. 1. Alternatively, shaft 100 may comprise an electrically conducting material, usually metal, which is selected from the group comprising tungsten, stainless steel alloys, platinum or its alloys, titanium or its alloys, molybdenum or its alloys, and nickel or its alloys. In this embodiment, shaft 100 includes an electrically insulating jacket, which is typically formed as one or more electrically insulating sheaths or coatings, such as polytetrafluoroethylene, polyimide, and the like. The provision of the electrically insulating jacket over the shaft prevents direct electrical contact between these metal elements and any adjacent body structure or the surgeon. Such direct electrical contact between a body structure (e.g., tendon) and an exposed electrode could result in unwanted heating and necrosis of the structure at the point of contact causing necrosis.

Handle 204 typically comprises a plastic material that is easily molded into a suitable shape for handling by the surgeon. Handle 204 defines an inner cavity (not shown) that houses the electrical connections 250 (FIG. 5), and provides a suitable interface for connection to an electrical connecting cable 22 (see FIG. 1). Electrode support member 102 extends from the distal end of shaft 100 (usually about 1 to 20 mm), and provides support for a plurality of electrically isolated electrode terminals 104 (see FIGS. 3 and 4). As shown in FIG. 2, a fluid tube 233 extends through an opening in handle 204, and includes a connector 235 for connection to a fluid supply source, for supplying electrically conductive fluid to the target site. Depending on the configuration of the distal surface of shaft 100, fluid tube 233 may extend through a single lumen (not shown) in shaft 100, or it may be coupled to a plurality of lumens (also not shown) that extend through shaft 100 to a plurality of openings at its distal end. In the representative embodiment, fluid tube 233 extends along the exterior of shaft 100 to a point just proximal of return electrode 112 (see FIG. 4). In this embodiment, the fluid is directed through an opening 237 past return electrode 112 to the electrode terminals 104. Probe 90 may also include a valve 17 (FIG. 1) or equivalent structure for controlling the flow rate of the electrically conducting fluid to the target site.

As shown in FIG. 2, the distal portion of shaft 100 is preferably bent to improve access to the operative site of the tissue being treated. Electrode support member 102 has a substantially planar tissue treatment surface 212 (FIG. 3) that is usually at an angle of about 10 to 90 degrees relative to the longitudinal axis of shaft 100, although the shaft may have no angle at all. In alternative embodiments, the distal portion of shaft 100 comprises a flexible material which can be deflected relative to the longitudinal axis of the shaft. Such deflection may be selectively induced by mechanical tension of a pull wire, for example, or by a shape memory wire that expands or contracts by externally applied temperature changes.

In the embodiment shown in FIGS. 2–5, probe 90 includes a return electrode 112 for completing the current path between electrode terminals 104 and a high frequency power supply 28 (see FIG. 1). As shown, return electrode 112 preferably comprises an annular conductive band coupled to the distal end of shaft 100 slightly proximal to tissue treatment surface 212 of electrode support member 102, typically about 0.5 to 10 mm and more preferably about 1 to 10 mm. In embodiments where the shaft comprises a conductive material, the shaft will have an exposed portion that functions as the return electrode. Return electrode 112 is coupled to a connector (not shown) that extends to the proximal end of probe 10, where it is suitably connected to power supply 10 (FIG. 1).

As shown in FIG. 2, return electrode 112 is not directly connected to electrode terminals 104. To complete this current path so that electrode terminals 104 are electrically connected to return electrode 112, electrically conducting fluid (e.g., isotonic saline) is caused to flow therebetween. In the representative embodiment, the electrically conducting fluid is delivered through fluid tube 233 to opening 237, as described above. Alternatively, the fluid may be delivered by a fluid delivery element (not shown) that is separate from probe 90. In arthroscopic surgery, for example, the body cavity will be flooded with isotonic saline and the probe 90 will be introduced into this flooded cavity. Electrically conducting fluid will be continually resupplied to maintain the conduction path between return electrode 112 and electrode terminals 104.

Figure 6:
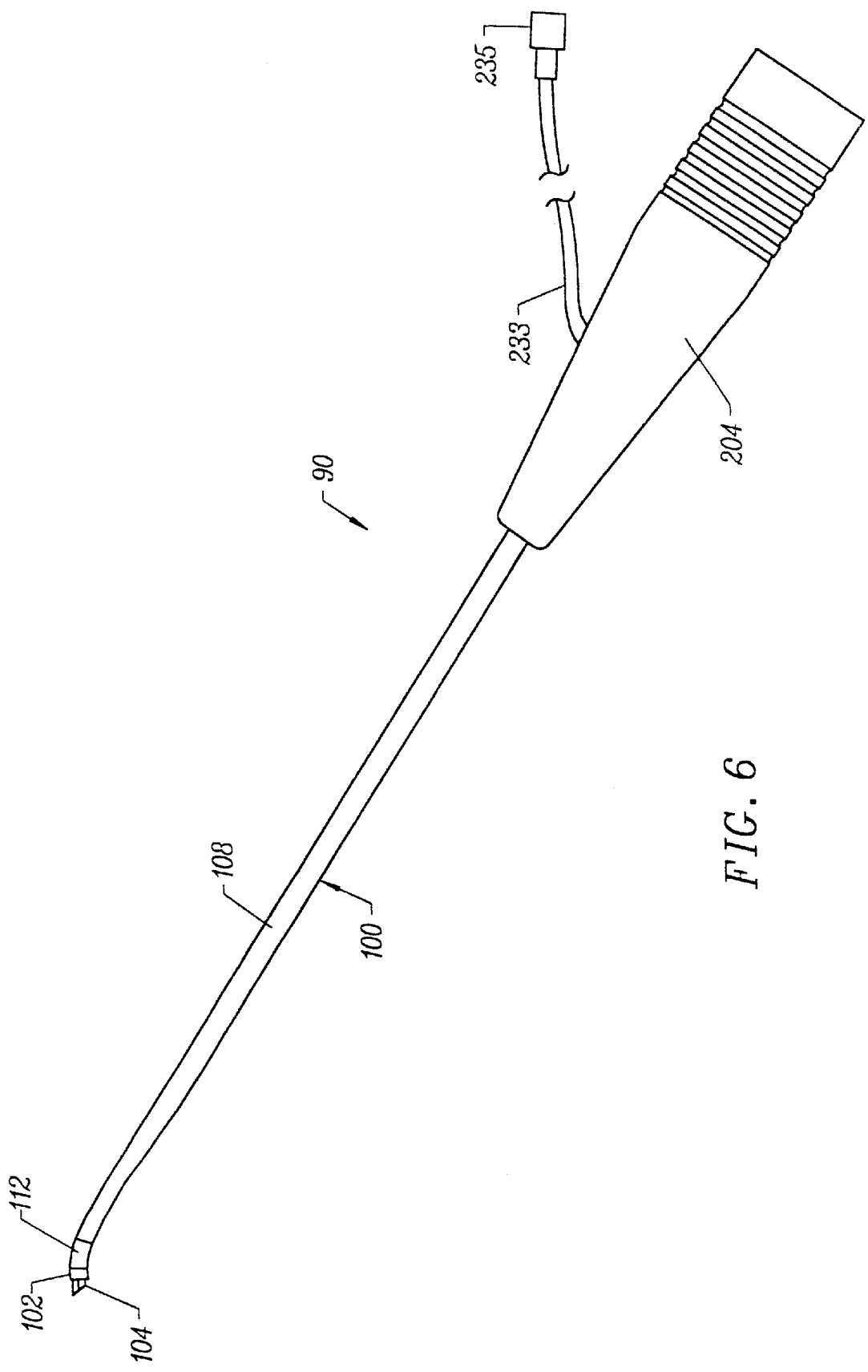
FIG. 6 is a perspective view of an alternative electrosurgical probe incorporating an inner fluid lumen.

In alternative embodiments, the fluid path may be formed in probe 90 by, for example, an inner lumen or an annular gap between the return electrode and a tubular support member within shaft 100 (see FIG. 6). This annular gap may be formed near the perimeter of the shaft 100 such that the electrically conducting fluid tends to flow radially inward towards the target site, or it may be formed towards the center of shaft 100 so that the fluid flows radially outward. In both of these embodiments, a fluid source (e.g., a bag of fluid elevated above the surgical site or suitable pumping device), is coupled to probe 90 via a fluid supply tube (not shown) that may or may not have a controllable valve.

Figure 3:
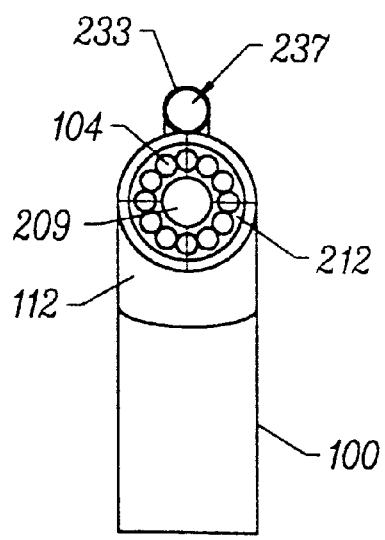
FIG. 3 is an end view of the probe of FIG. 2.
Figure 4:
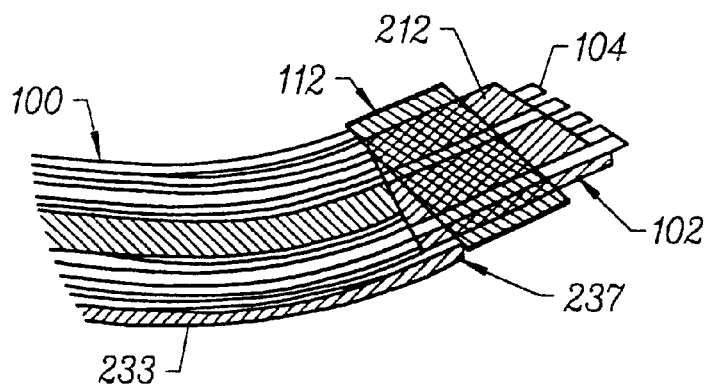
FIG. 4 is a cross sectional view of the electrosurgical probe of FIG. 1.

Referring to FIG. 3, the electrically isolated electrode terminals 104 are spaced apart over tissue treatment surface 212 of electrode support member 102. The tissue treatment surface and individual electrode terminals 104 will usually have dimensions within the ranges set forth above. In the representative embodiment, the tissue treatment surface 212 has a circular cross-sectional shape with a diameter in the range of about 1 to 20 mm. The individual electrode terminals 104 preferably extend outward from tissue treatment surface 212 by a distance of about 0.0 to 4 mm, usually about 0.2 to 2 mm. Applicant has found that this configuration increases the high electric field intensities and associated current densities around electrode terminals 104 to facilitate the ablation of tissue as described in detail above.

In the embodiment of FIGS. 2–5, the probe includes a single, larger opening 209 in the center of tissue treatment surface 212, and a plurality of electrode terminals (e.g., about 3 to 15 electrode terminals) around the perimeter of surface 212 (see FIG. 3). Alternatively, the probe may include a single, annular, or partially annular, electrode terminal at the perimeter of the tissue treatment surface. The central opening 209 is coupled to a suction lumen 215 within shaft 100 and a suction tube 211 (FIG. 2) for aspirating tissue, fluids, and/or gases from the target site. In this embodiment, the electrically conductive fluid generally flows radially inward past electrode terminals 104 and then back through the opening 209. Aspirating the electrically conductive fluid during surgery allows the surgeon to see the target site, and it prevents the dispersal of gases, tissue fragments and/or calcified deposits into the patient's body.

In some embodiments, the probe 90 will also include one or more aspiration electrode(s) (not shown) coupled to the aspiration lumen 215 for inhibiting clogging during aspiration of tissue fragments from the surgical site. A more complete description of these embodiments can be found in commonly assigned co-pending application Ser. No. 09/010, 382, filed Jan. 21, 1998, the complete disclosure of which is incorporated herein by reference for all purposes.

Figure 5:
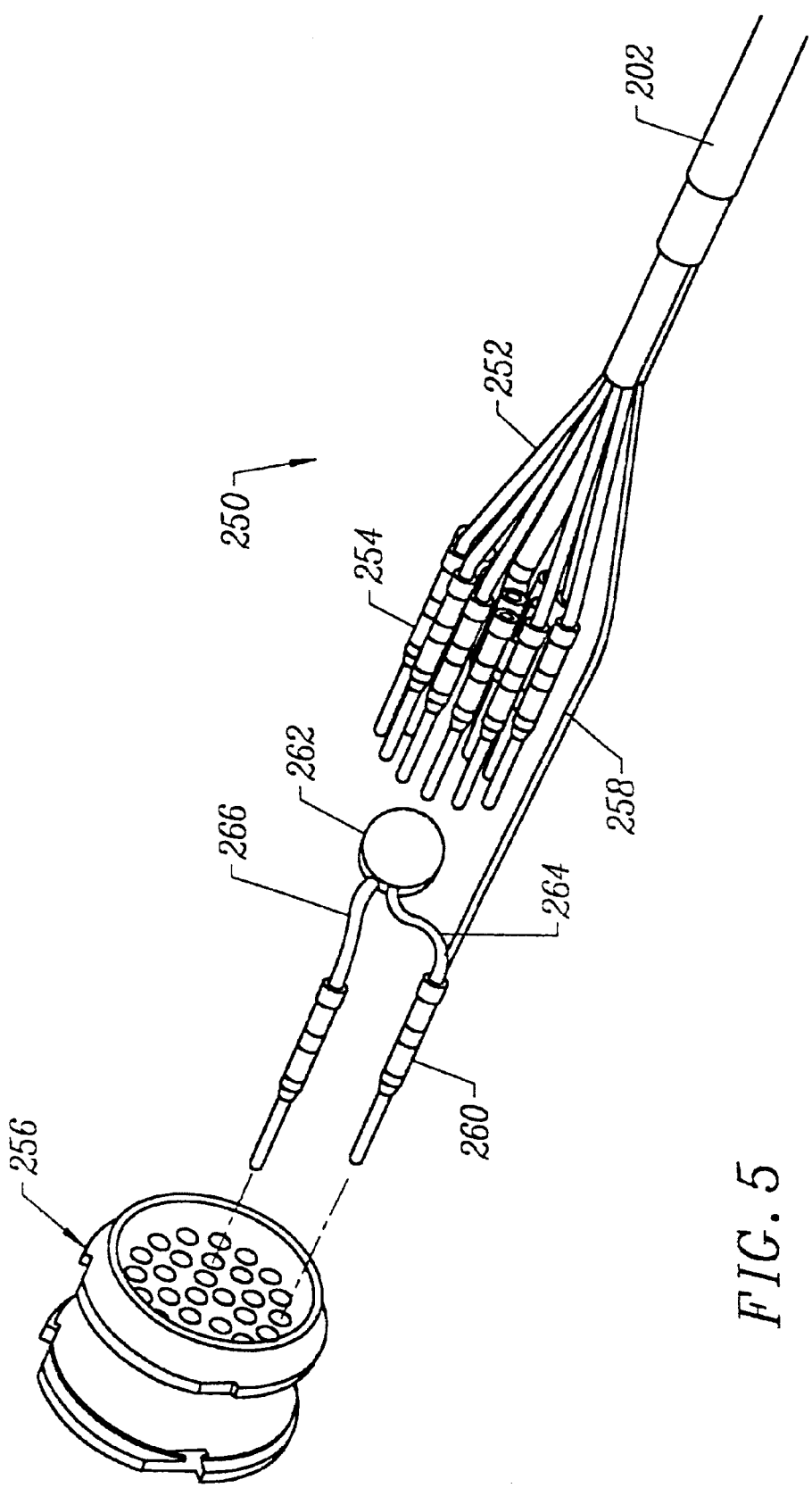
FIG. 5 is an exploded view of a proximal portion of the electrosurgical probe.

FIG. 5 illustrates the electrical connections 250 within handle 204 for coupling electrode terminals 104 and return electrode 112 to the power supply 28. As shown, a plurality of wires 252 extend through shaft 100 to couple terminals 104 to a plurality of pins 254, which are plugged into a connector block 256 for coupling to a connecting cable 22 (FIG. 1). Similarly, return electrode 112 is coupled to connector block 256 via a wire 258 and a pin 260.

According to the present invention, the probe 90 further includes an identification element that is characteristic of the particular electrode assembly so that the same power supply 28 can be used for different electrosurgical operations. In one embodiment, for example, the probe 90 includes a voltage reduction element or a voltage reduction circuit for reducing the voltage applied between the electrode terminals 104 and the return electrode 112. The voltage reduction element serves to reduce the voltage applied by the power supply so that the voltage between the electrode terminals and the return electrode is low enough to avoid excessive power dissipation into the electrically conducting medium and/or ablation of the soft tissue at the target site. The voltage reduction element primarily allows the electrosurgical probe 90 to be compatible with other ArthroCare generators that are adapted to apply higher voltages for ablation or vaporization of tissue. For contraction of tissue, for example, the voltage reduction element will serve to reduce a voltage of about 100 to 135 volts rms (which is a setting of 1 on the ArthroCare Models 970, 980 and 2000 Generators) to about 45 to 60 volts rms, which is a suitable voltage for contraction of tissue without ablation (e.g., molecular dissociation) of the tissue.

Of course, for some procedures, the probe will typically not require a voltage reduction element. Alternatively, the probe may include a voltage increasing element or circuit, if desired.

In the representative embodiment, the voltage reduction element is a dropping capacitor 262 which has first leg 264 coupled to the return electrode wire 258 and a second leg 266 coupled to connector block 256. Of course, the capacitor may be located in other places within the system, such as is in, or distributed along the length of: (1) the cable; (2) in the generator; (3) in the connector, etc. In addition, it will be recognized that other voltage reduction elements, such as diodes, transistors, inductors, resistors, capacitors or combinations thereof, may be used in conjunction with the present invention. For example, the probe 90 may include a coded resistor (not shown) that is constructed to lower the voltage applied between return electrode 112 and electrode terminals 104 to a suitable level for contraction of tissue. In addition, electrical circuits may be employed for this purpose.

Alternatively or additionally, the cable 22 that couples the power supply 10 to the probe 90 may be used as a voltage reduction element. The cable has an inherent capacitance that can be used to reduce the power supply voltage if the cable is placed into the electrical circuit between the power supply, the electrode terminals and the return electrode. In this embodiment, the cable 22 may be used alone, or in combination with one of the voltage reduction elements discussed above, e.g., a capacitor.

Further, it should be noted that the present invention can be used with a power supply that is adapted to apply a voltage within the selected range for treatment of tissue. In this embodiment, a voltage reduction element or circuitry may not be desired.

Figure 7A:
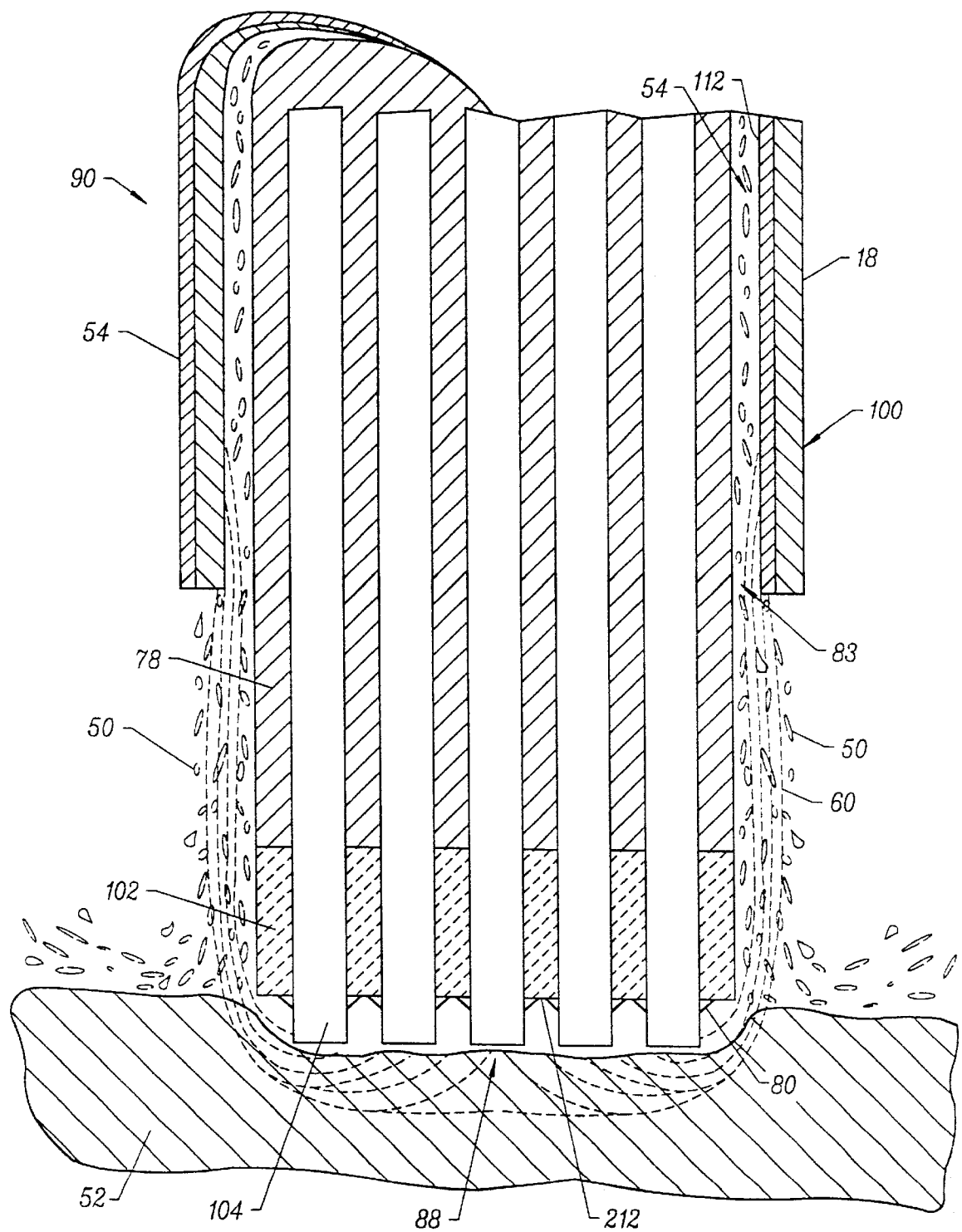
FIGS. 7A–7C are cross-sectional views of the distal portions of three different embodiments of an electrosurgical probe according to the present invention.
Figure 7B:
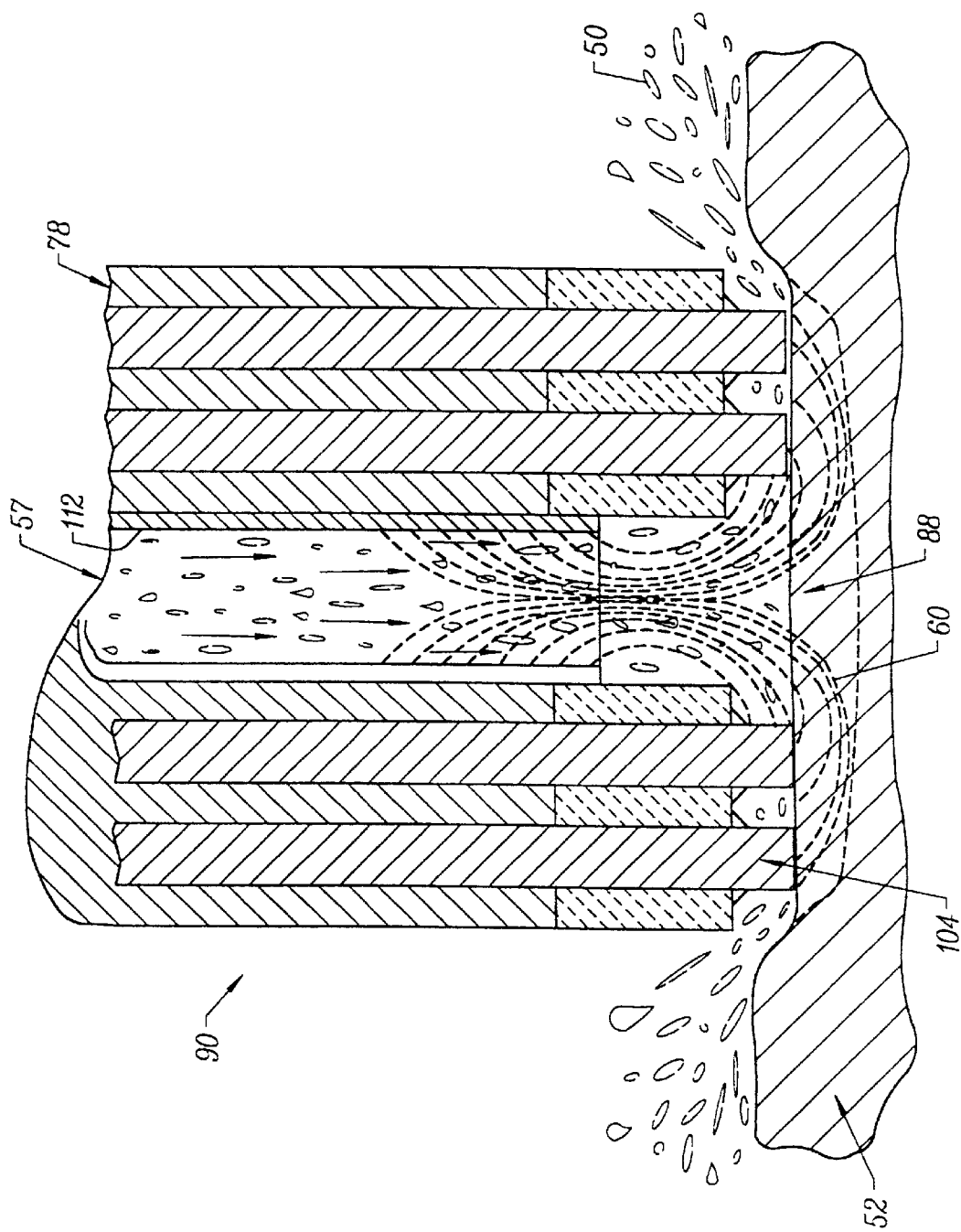
Figure 7C:
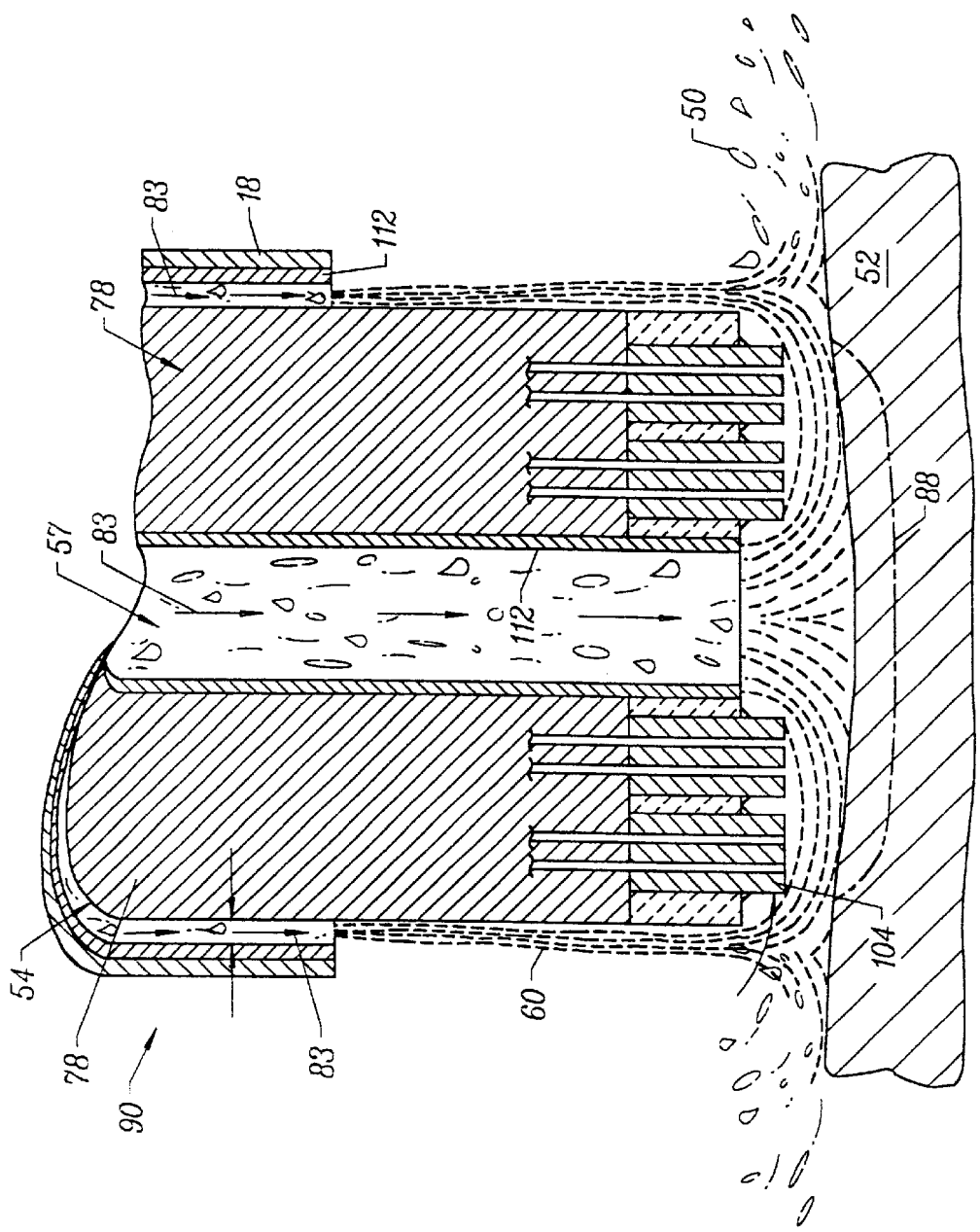

FIGS. 7A–7C schematically illustrate the distal portion of three different embodiments of probe 90 according to the present invention. As shown in 7A, electrode terminals 104 are anchored in a support matrix 102 of suitable insulating material (e.g., ceramic or glass material, such as alumina, silicon nitride zirconia and the like) which could be formed at the time of manufacture in a flat, hemispherical or other shape according to the requirements of a particular procedure. The preferred support matrix material is alumina, available from Kyocera Industrial Ceramics Corporation, Elkgrove, Ill., because of its high thermal conductivity, good thermal shock resistance, good electrically insulative properties, high flexural modulus, resistance to carbon tracking, biocompatibility, and high melting point. The support matrix 102 is adhesively joined to a tubular support member 78 that extends most or all of the distance between matrix 102 and the proximal end of probe 90. Tubular member 78 preferably comprises an electrically insulating material, such as an epoxy or silicone-based material.

In a preferred construction technique, electrode terminals 104 extend through pre-formed openings in the support matrix 102 so that they protrude above tissue treatment surface 212 by the desired distance. The electrodes are then bonded to the tissue treatment surface 212 of support matrix 102, typically by an inorganic sealing material 80. Sealing material 80 is selected to provide effective electrical insulation, and good adhesion to both the alumina matrix 102 and the electrode terminals (e.g., titanium, tungsten, molybdenum, platinum, etc.). Sealing material 80 additionally should have a compatible thermal expansion coefficient and a melting point well below that of the metal electrode terminals and the ceramic support matrix, typically being a glass or glass ceramic.

In the embodiment shown in FIG. 7A, return electrode 112 comprises an annular member positioned around the exterior of shaft 100 of probe 90. Return electrode 90 may fully or partially circumscribe tubular support member 78 to form an annular gap 54 therebetween for flow of electrically conducting fluid 50 therethrough, as discussed below. Gap 54 preferably has a width in the range of 0.1 mm to 4 mm. Alternatively, probe may include a plurality of longitudinal ribs between support member 78 and return electrode 112 to form a plurality of fluid lumens extending along the perimeter of shaft 100. In this embodiment, the plurality of lumens will extend to a plurality of openings.

Return electrode 112 is disposed within an electrically insulative jacket 18, which is typically formed as one or more electrically insulative sheaths or coatings, such as polytetrafluoroethylene, polyamide, and the like. The provision of the electrically insulative jacket 18 over return electrode 112 prevents direct electrical contact between return electrode 112 and any adjacent body structure. Such direct electrical contact between a body structure (e.g., tendon) and an exposed electrode member 112 could result in unwanted heating and necrosis of the structure at the point of contact causing necrosis.

As shown in FIG. 7A, return electrode 112 is not directly connected to electrode terminals 104. To complete this current path so that terminals 104 are electrically connected to return electrode 112, electrically conducting fluid 50 (e.g., isotonic saline) is caused to flow along fluid path(s) 83. Fluid path 83 is formed by annular gap 54 between outer return electrode 112 and tubular support member 78. The electrically conducting fluid 50 flowing through fluid path 83 provides a pathway for electrical current flow between electrode terminals 104 and return electrode 112, as illustrated by the current flux lines 60 in FIG. 6A. When a voltage difference is applied between electrode terminals 104 and return electrode 112, high electric field intensities will be generated at the distal tips of terminals 104 with current flow from terminals 104 through the target tissue to the return electrode, the high electric field intensities causing ablation of tissue 52 in zone 88.

FIG. 7B illustrates another alternative embodiment of electrosurgical probe 90 which has a return electrode 112 positioned within tubular member 78. Return electrode 112 is preferably a tubular member defining an inner lumen 57 for allowing electrically conducting fluid 50 (e.g., isotonic saline) to flow therethrough in electrical contact with return electrode 112. In this embodiment, a voltage difference is applied between electrode terminals 104 and return electrode 112 resulting in electrical current flow through the electrically conducting fluid 50 as shown by current flux lines 60 (FIG. 3). As a result of the applied voltage difference and concomitant high electric field intensities at the tips of electrode terminals 104, tissue 52 becomes ablated or transected in zone 88.

FIG. 7C illustrates another embodiment of probe 90 that is a combination of the embodiments in FIGS. 7A and 7B. As shown, this probe includes both an inner lumen 57 and an outer gap or plurality of outer lumens 54 for flow of electrically conductive fluid. In this embodiment, the return electrode 112 may be positioned within tubular member 78 as in FIG. 7B, outside of tubular member 78 as in FIG. 7A, or in both locations.

Figure 8:
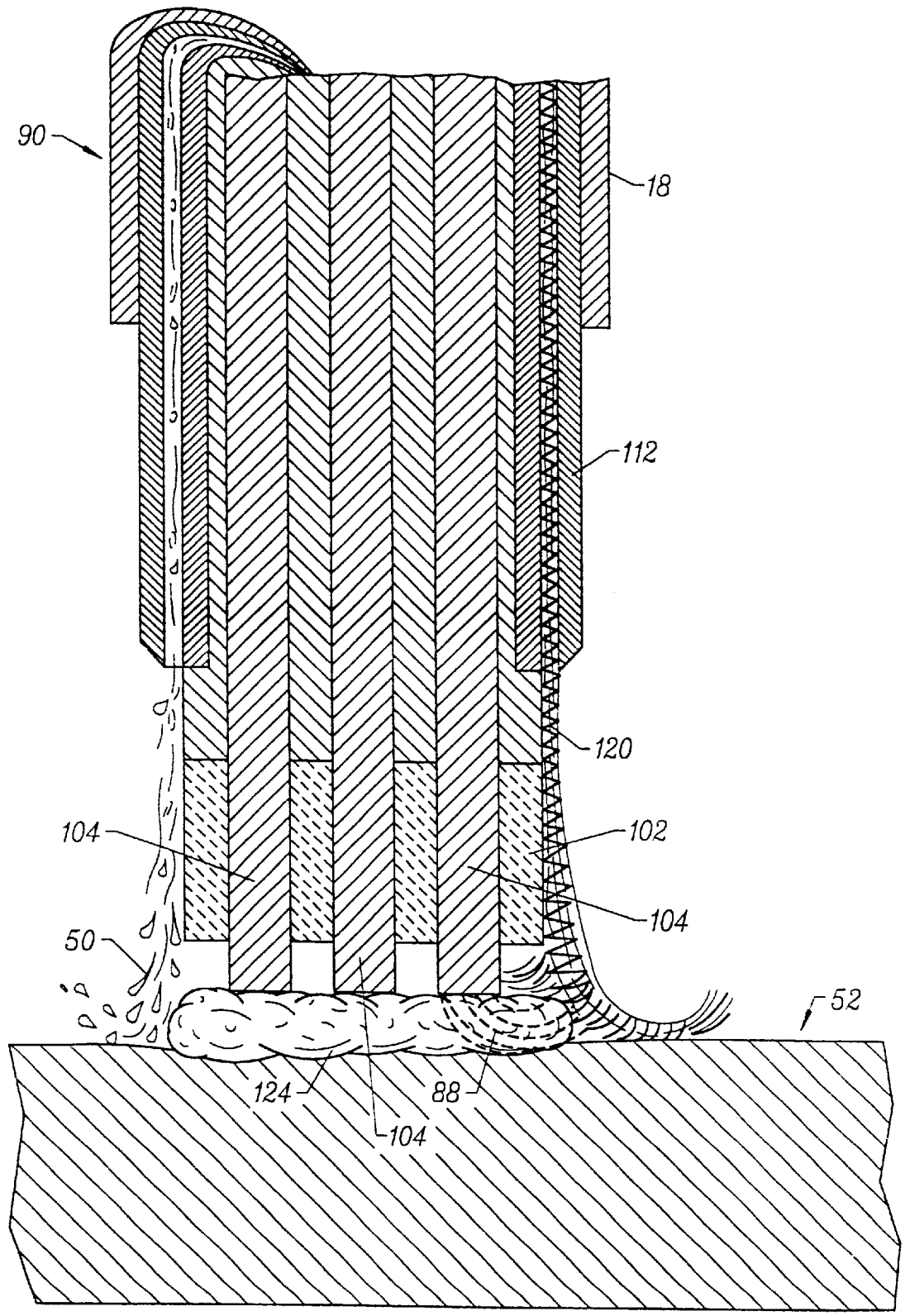
FIG. 8 is a cross-sectional view of the distal tip of an electrosurgical probe, illustrating electric field lines between the active and return electrodes.
Figure 9:
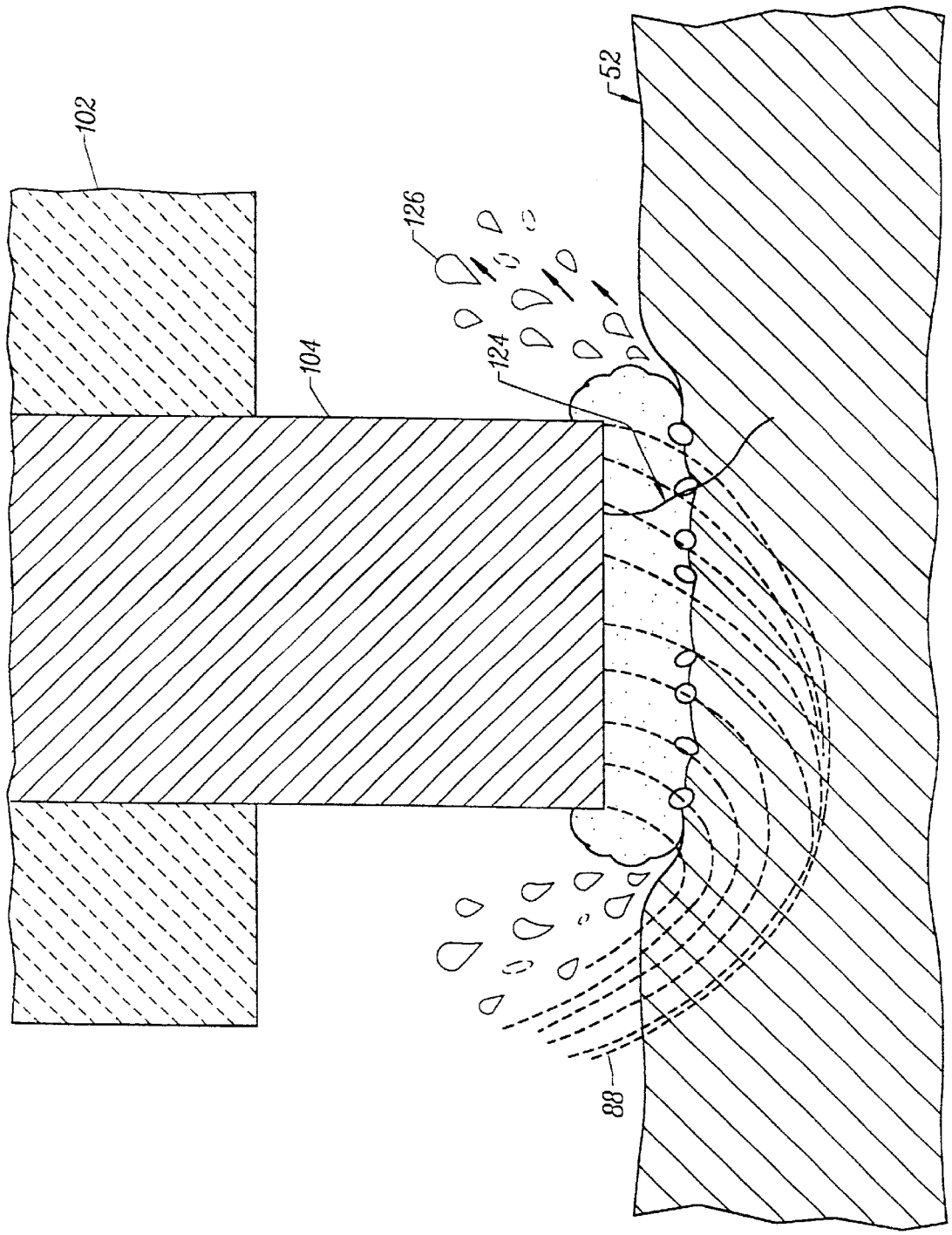
FIG. 9 is an enlarged cross-sectional view of the distal tip of an electrosurgical probe, illustrating a vapor layer formed between the active electrodes and the target tissue.

FIG. 8 illustrates the current flux lines associated with an electric field 120 applied between the active and return electrodes 104, 112 when a voltage is applied therebetween. As shown, the electric field intensity is substantially higher in the region 88 at the tip of the electrode 58 because the current flux lines are concentrated in these regions. This high electric field intensity leads to induced molecular breakdown of the target tissue through molecular dissociation. As a result of the applied voltage difference between electrode terminal(s) 104 and the target tissue 52(i.e., the voltage gradient across the plasma layer 124), charged particles (not shown) in the plasma (viz., electrons) are accelerated towards the tissue. At sufficiently high voltage differences, these charged particles gain sufficient energy to cause dissociation of the molecular bonds within tissue structures. This molecular dissociation is accompanied by the volumetric removal (i.e., ablative sublimation) of tissue and the production of low molecular weight gases 126 (see FIG. 9), such as oxygen, nitrogen, carbon dioxide, hydrogen and methane. The short range of the accelerated charged particles within the tissue confines the molecular dissociation process to the surface layer to minimize damage and necrosis to the underlying tissue.

Figure 10:
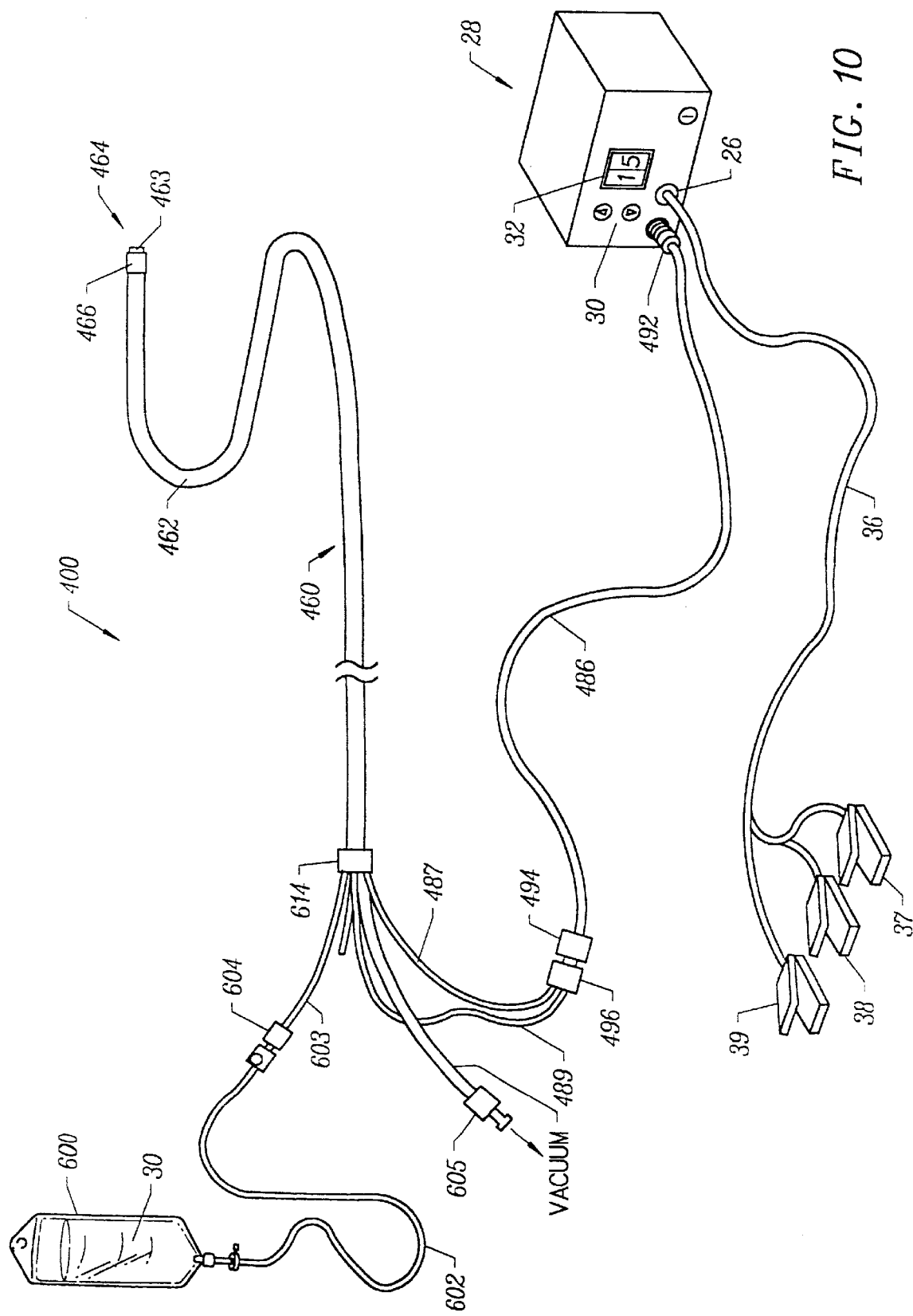
FIG. 10 is a perspective view of an electrosurgical catheter system for removing body structures according to the present invention.
Figure 11:
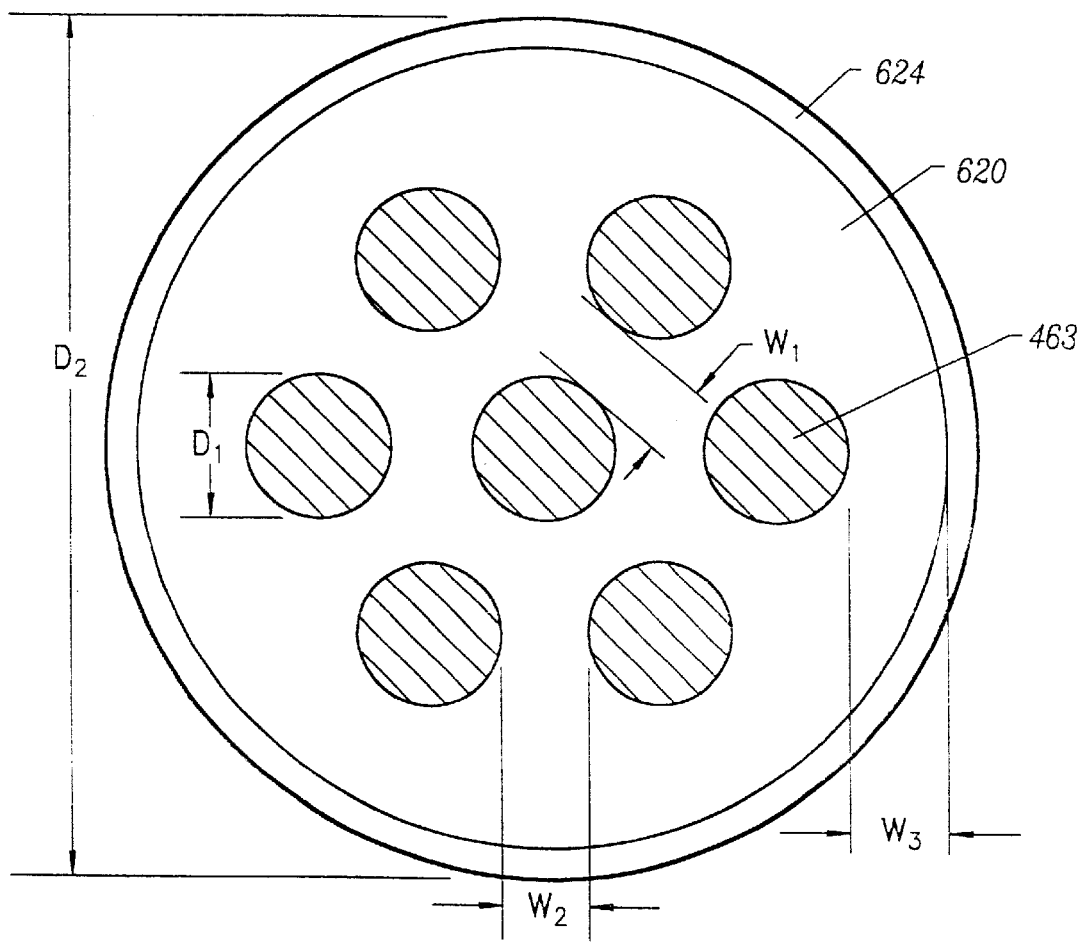
FIG. 11 illustrates the distal portion of an electrosurgical catheter for use with the system of FIG. 10.

Referring to FIGS. 10–12, the electrosurgical device according to the present invention may also be configured as an elongate catheter system 400 including portions with sufficient flexibility to permit introduction into the body and to the target site through one or more vascular lumen(s). As shown in FIG. 10, a catheter system 400 generally comprises an electrosurgical catheter 460 connected to a power supply 28 by an interconnecting cable 486 for providing high frequency voltage to a target tissue site and an irrigant reservoir or source 600 for providing electrically conducting fluid to the target site. Catheter 460 generally comprises an elongate, flexible shaft body 462 including a tissue removing or ablating region 464 at the distal end of body 462. The proximal portion of catheter 460 includes a multi-lumen fitment 614 which provides for interconnections between lumens and electrical leads within catheter 460 and conduits and cables proximal to fitment 614. By way of example, a catheter electrical connector 496 is removably connected to a distal cable connector 494 which, in turn, is removably connectable to generator 28 through connector 492. One or more electrically conducting lead wires (not shown) within catheter 460 extend between one or more active electrodes 463 at tissue ablating region 464 and one or more corresponding electrical terminals (also not shown) in catheter connector 496 via active electrode cable branch 487. Similarly, one or more return electrodes 466 at tissue ablating region 464 are coupled to a return electrode cable branch 489 of catheter connector 496 by lead wires (not shown). Of course, a single cable branch (not shown) may be used for both active and return electrodes.

Catheter body 462 may include reinforcing fibers or braids (not shown) in the walls of at least the distal ablation region 464 of body 462 to provide responsive torque control for rotation of electrode terminals during tissue engagement. This rigid portion of the catheter body 462 preferably extends only about 7 to 10 mm while the remainder of the catheter body 462 is flexible to provide good trackability during advancement and positioning of the electrodes adjacent target tissue.

Conductive fluid 30 is provided to tissue ablation region 464 of catheter 460 via a lumen (not shown in FIG. 10) within catheter 460. Fluid is supplied to lumen from the source along a conductive fluid supply line 602 and a conduit 603, which is coupled to the inner catheter lumen at multi-lumen fitment 614. The source of conductive fluid (e.g., isotonic saline) may be an irrigant pump system (not shown) or a gravity-driven supply, such as an irrigant reservoir 600 positioned several feet above the level of the patient and tissue ablating region 8. A control valve 604 may be positioned at the interface of fluid supply line 602 and conduit 603 to allow manual control of the flow rate of electrically conductive fluid 30. Alternatively, a metering pump or flow regulator may be used to precisely control the flow rate of the conductive fluid.

System 400 further includes an aspiration or vacuum system (not shown) to aspirate liquids and gases from the target site. The aspiration system will usually comprise a source of vacuum coupled to fitment 614 by a aspiration connector 605.

FIGS. 11 and 12 illustrate the working end 464 of an electrosurgical catheter 460 constructed according to the principles of the present invention. As shown in FIG. 11, catheter 460 generally includes an elongated shaft 462 which may be flexible or rigid, and an electrode support member 620 coupled to the distal end of shaft 462. Electrode support member 620 extends from the distal end of shaft 462 (usually about 1 to 20 mm), and provides support for a plurality of electrically isolated electrode terminals 463. Electrode support member 620 and electrode terminals 463 are preferably secured to a tubular support member 626 within shaft 460 by adhesive 630.

The electrode terminals 463 may be constructed using round, square, rectangular or other shaped conductive metals. By way of example, the electrode terminal materials may be selected from the group including stainless steel, tungsten and its alloys, molybdenum and its alloys, titanium and its alloys, nickel-based alloys, as well as platinum and its alloys. Electrode support member 620 is preferably a ceramic, glass or glass/ceramic composition (e.g., aluminum oxide, titanium nitride). Alternatively, electrode support member 620 may include the use of high-temperature biocompatible plastics such as polyether-ether-keytone (PEEK) manufactured by Vitrex International Products, Inc. or polysulfone manufactured by GE Plastics. The adhesive 630 may, by way of example, be an epoxy (e.g., Master Bond EP42HT manufactured by Master Bond) or a silicone-based adhesive.

Figure 12A:
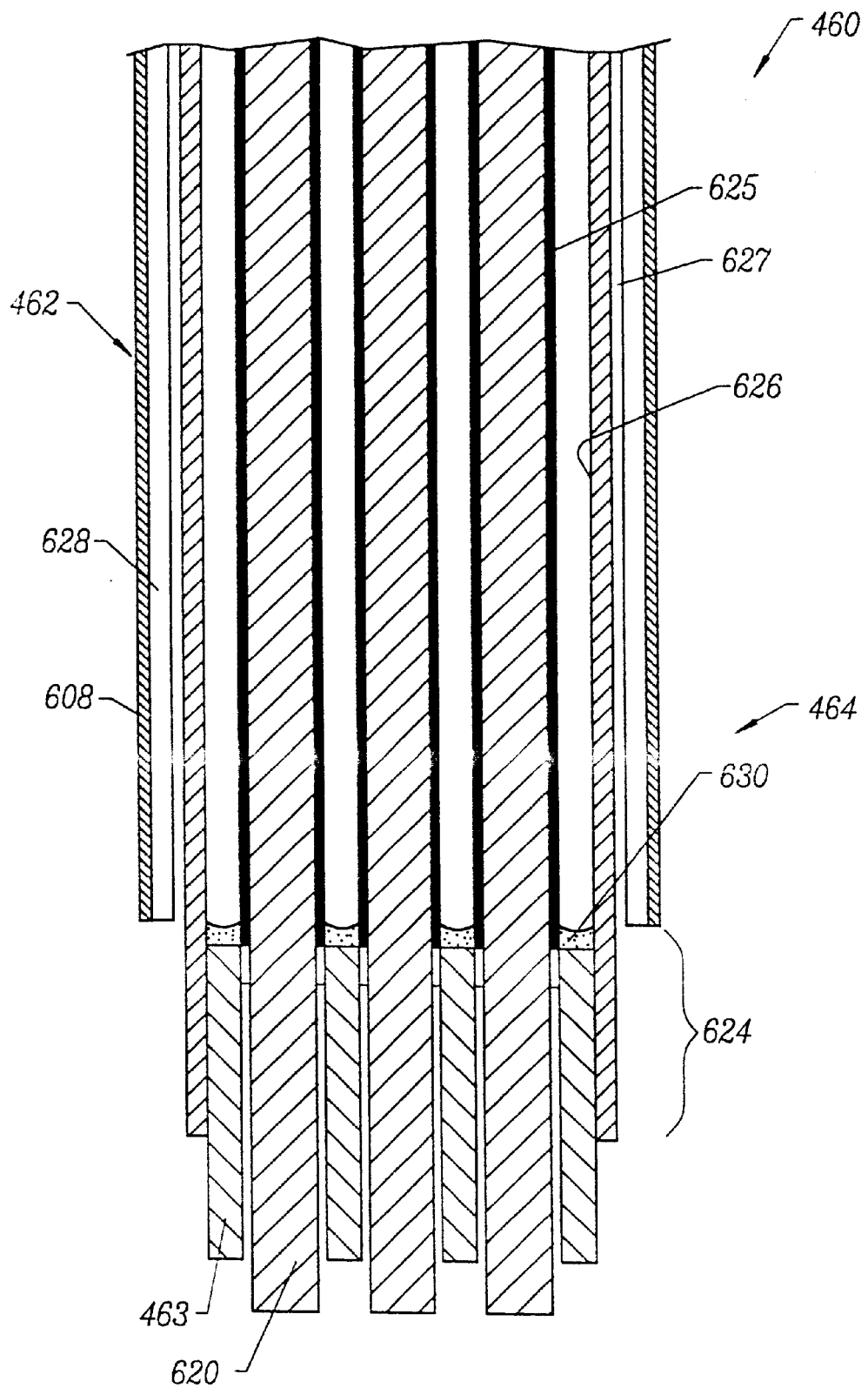
FIG. 12A and 12B are cross-sectional and end views, respectively of a distal portion of a second electrosurgical catheter according to the present invention.
Figure 12B:
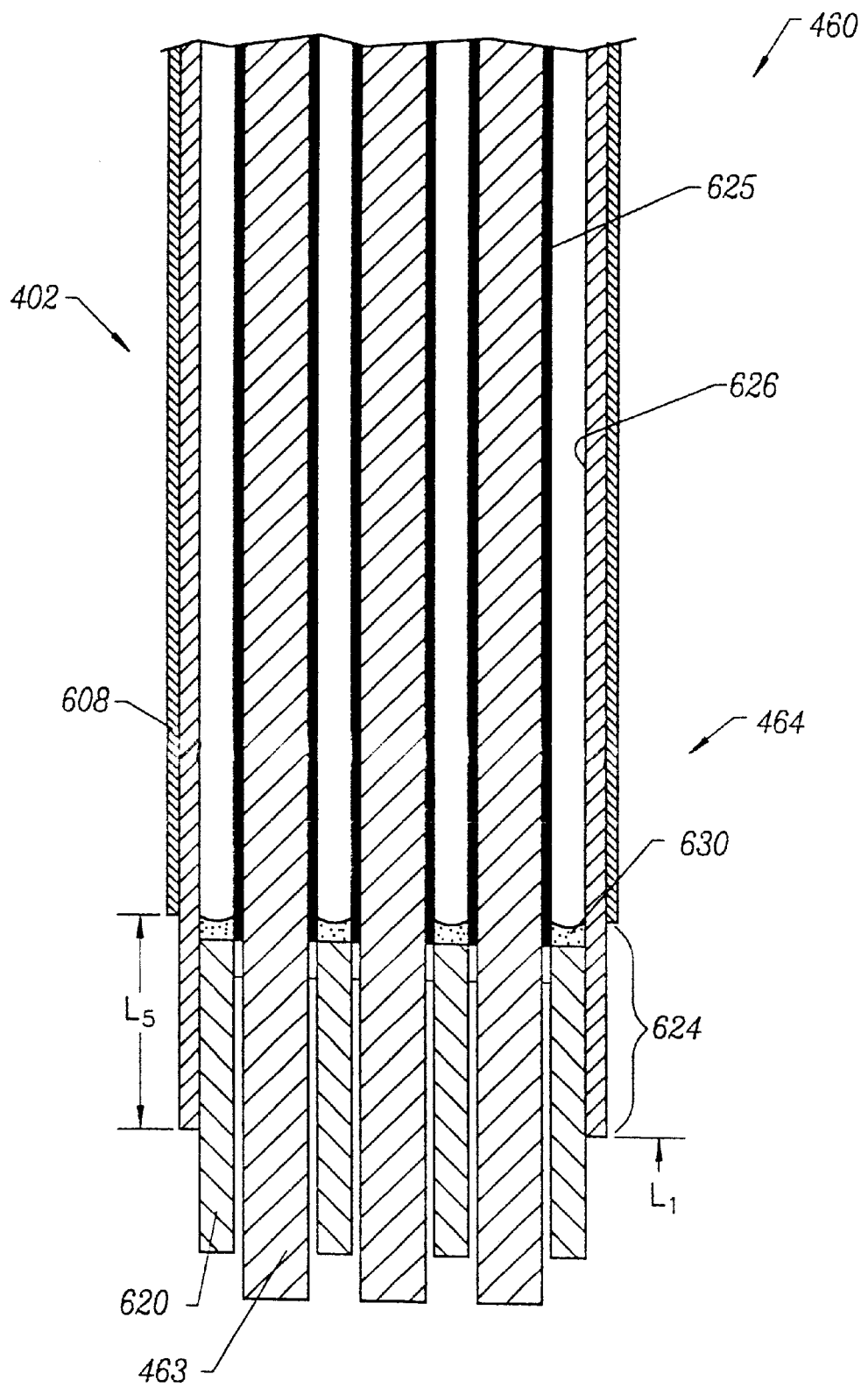

As shown in FIG. 12B, a total of 7 circular active electrodes or electrode terminals 463 are shown in a symmetrical pattern having an active electrode diameter, $D_1$ in the range from 0.05 mm to 1.5 mm, more preferably in the range from 0.1 mm to 0.75 mm. The interelectrode spacings, $W_1$ and $W_2$ are preferably in the range from 0.1 mm to 1.5 mm and more preferably in the range from 0.2 mm to 0.75 mm. The distance between the outer perimeter of the electrode terminal 463 and the perimeter of the electrode support member, $W_3$ is preferably in the range from 0.1 mm to 1.5 mm and more preferably in the range from 0.2 mm to 0.75 mm. The overall diameter, $D_2$ of the working end 464 of catheter body 462 is preferably in the range from 0.5 mm to 10 mm and more preferably in the range from 0.5 mm to 5 mm. As discussed above, the shape of the active electrodes may be round, square, triangular, hexagonal, rectangular, tubular, flat strip and the like and may be arranged in a circularly symmetric pattern as shown in FIG. 12B or may, by way of example, be arranged in a rectangular pattern, square pattern, or strip.

Catheter body 462 includes a tubular cannula 626 extending along body 462 radially outward from support member 620 and electrode terminals 463. The material for cannula 626 may be advantageously selected from a group of electrically conductive metals so that the cannula 626 functions as both a structural support member for the array of electrode terminals 463 as well as a return electrode 624. The support member 626 is connected to an electrical lead wire (not shown) at its proximal end within a connector housing (not shown) and continues via a suitable connector to power supply 28 to provide electrical continuity between one output pole of high frequency generator 28 and said return electrode 624. The cannula 626 may be selected from the group including stainless steel, copper-based alloys, titanium or its alloys, and nickel-based alloys. The thickness of the cannula 626 is preferably in the range from 0.08 mm to 1.0 mm and more preferably in the range from 0.05 mm to 0.4 mm.

As shown in FIGS. 11 and 12A, cannula 626 is covered with an electrically insulating sleeve 608 to protect the patient's body from the electric current. Electrically insulating sleeve 608 may be a coating (e.g., nylon) or heat shrinkable plastic (e.g., fluropolymer or polyester). As shown in FIG. 12A, the proximal portion of the cannula 626 is left exposed to function as the return electrode 624. The length of the return electrode 624, $L_5$ is preferably in the range from 1 mm to 30 mm and more preferably in the range from 2 mm to 20 mm. The spacing between the most distal portion of the return electrode 624 and the plane of the tissue treatment surface 622 of the electrode support member 620, $L_1$ is preferably in the range from 0.5 mm to 30 mm and more preferably in the range from 1 mm to 20 mm. The thickness of the electrically insulating sleeve 608 is preferably in the range from 0.01 mm to 0.5 mm and more preferably in the range from 0.02 mm to 0.2 mm.

In the embodiment shown in FIG. 11, the fluid path is formed in catheter by an inner lumen 627 or annular gap between the return electrode 624 and a second tubular support member 628 within shaft 460. This annular gap may be formed near the perimeter of the shaft 460 as shown in FIG. 11 such that the electrically conducting fluid tends to flow radially inward towards the target site, or it may be formed towards the center of shaft 460 (not shown) so that the fluid flows radially outward. In both of these embodiments, a fluid source (e.g., a bag of fluid elevated above the surgical site or having a pumping device), is coupled to catheter 460 via a fluid supply tube (not shown) that may or may not have a controllable valve.

In an alternative embodiment shown in FIG. 12A, the electrically conducting fluid is delivered from a fluid delivery element (not shown) that is separate from catheter 460. In arthroscopic surgery, for example, the body cavity will be flooded with isotonic saline and the catheter 460 will be introduced into this flooded cavity. Electrically conducting fluid will be continually resupplied to maintain the conduction path between return electrode 624 and electrode terminals 463.

Figure 13:
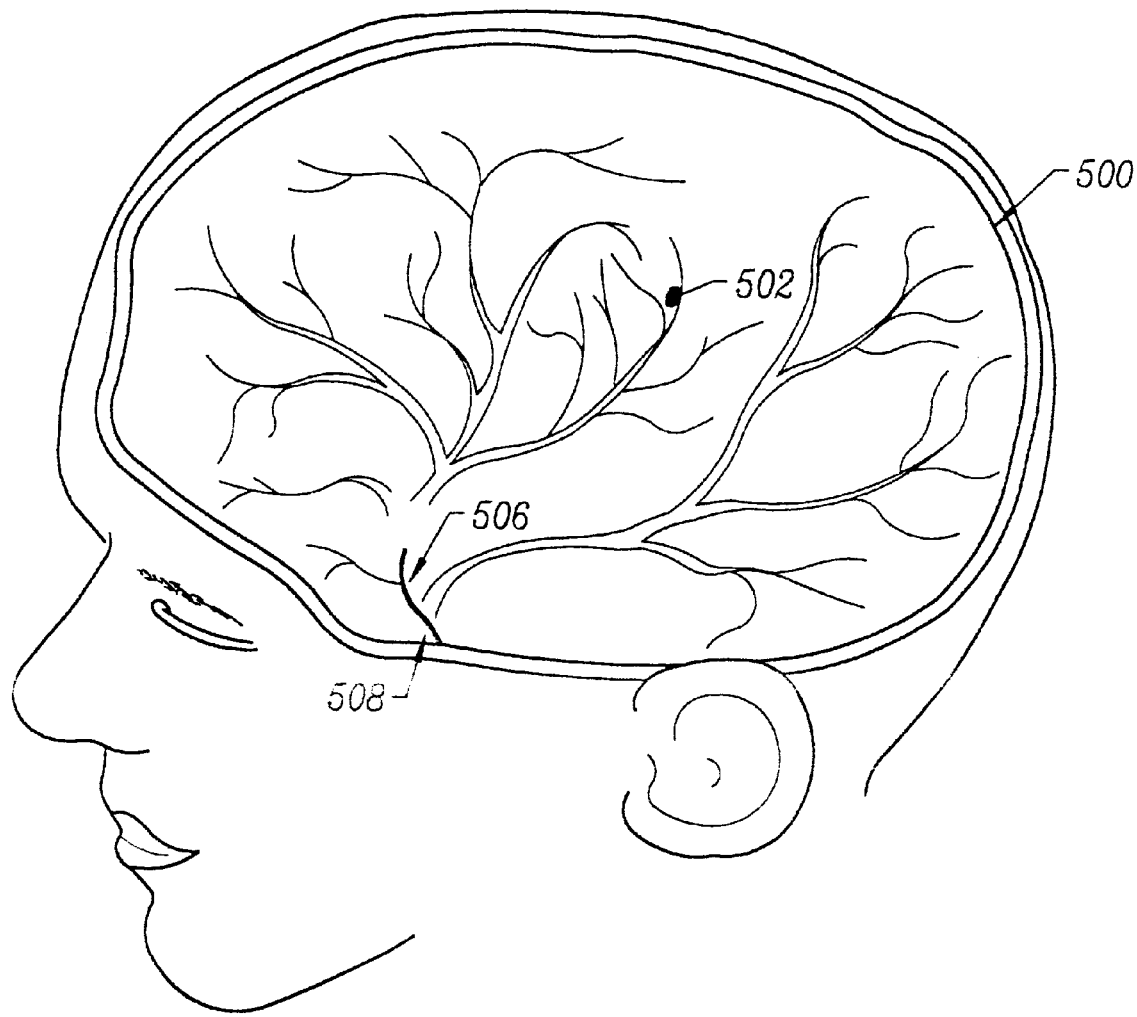
FIG. 13 illustrates a method of treating a blood vessel in the brain according to the present invention.
Figure 14:
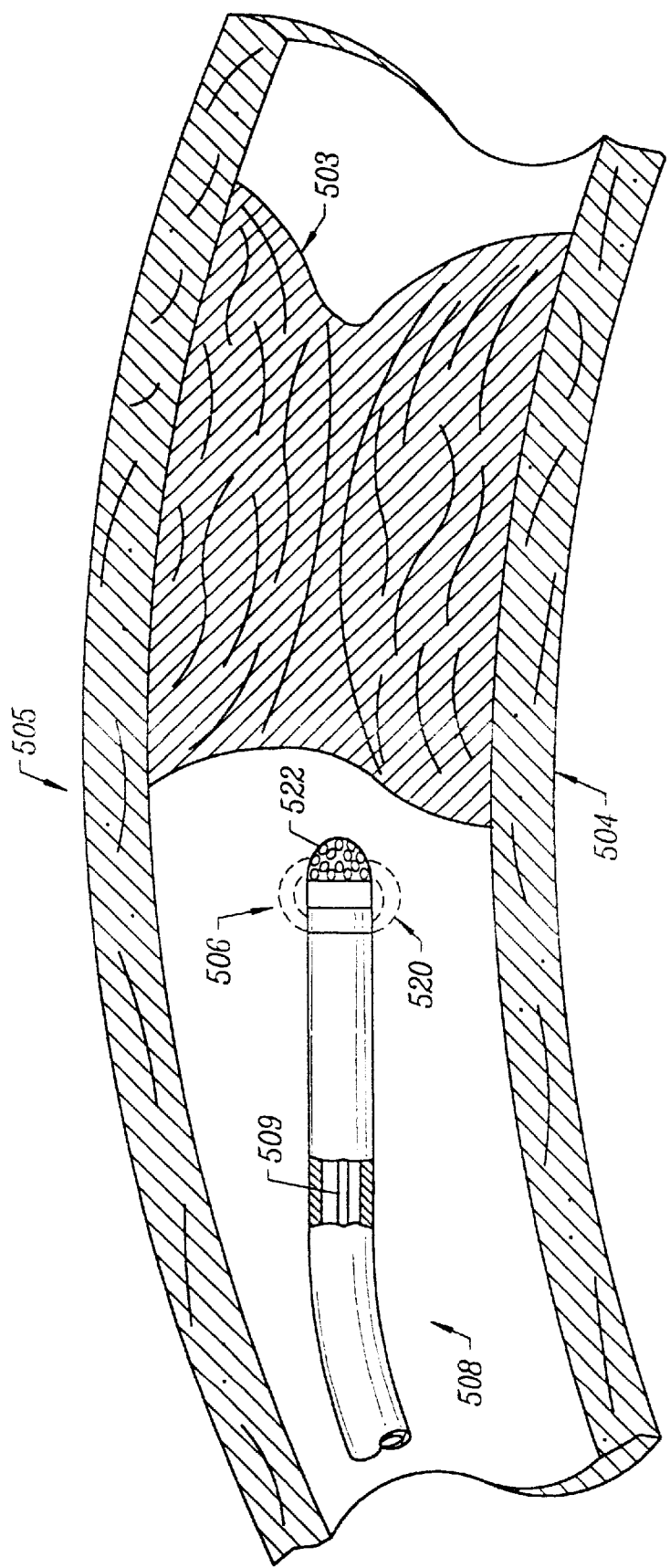
FIG. 14 illustrates a method of removing occlusive media within a blood vessel in the brain.

FIGS. 13 and 14 illustrate a method for treating cerebrovascular disease according to the present invention. Typically, a distal portion 506 of an electrosurgical catheter 508 such as the one described above is percutaneously introduced into the vasculature and endoluminally advanced into the patient's brain 500. The catheter 508 may be guided to the target location 502 within the patient's brain using any number of conventional or non-conventional techniques (e.g., sterotactic systems) as described above. The catheter 508 may be advanced with a variety of techniques, such as a guidewire, steerable catheter and the like. Referring now to FIG. 14, a severe occlusion 503 in a body passage 505 often completely or partially blocks the body passage, making it extremely difficult to recanalize with conventional catheter techniques. In these circumstances, it is necessary to at least partially recanalize (creating an opening through) the occlusion before conventional catheter procedures can begin. Conventional methods for recanalizing severe occlusions include hot-tipped catheters, laser catheters, and drill-tipped catheters. These approaches rely on very aggressive treatment of the stenotic material, which can expose the blood vessel wall to significant injury, for example, vessel perforation.

Once the surgeon has reached the point of major blockage 503, electrically conductive fluid is delivered through one or more internal lumen(s) 509 within the catheter to the tissue. In some embodiments, the catheter may be configured to operate with a naturally occurring body fluid, e.g., blood, as the conductive medium. The fluid flows past the return electrode 520 to the electrode terminals 522 at the distal end of the catheter shaft. The rate of fluid flow is controlled with a valve (not shown) such that the zone between the occlusion and electrode terminal(s) 522 is constantly immersed in the fluid. The power supply 28 (FIG. 10) is then turned on and adjusted such that a high frequency voltage difference is applied between electrode terminals 522 and return electrode 520. The electrically conductive fluid provides the conduction path (see current flux lines) between electrode terminals 522 and the return electrode 520.

As discussed above, the high frequency voltage is sufficient to convert the electrically conductive fluid (not shown) between the occlusion 503 and electrode terminal(s) 522 into an ionized vapor layer or plasma (not shown). As a result of the applied voltage difference between electrode terminal(s) 522 and the occlusive media 503 (i.e., the voltage gradient across the plasma layer), charged particles in the plasma (viz., electrons) are accelerated towards the occlusion. At sufficiently high voltage differences, these charged particles gain sufficient energy to cause dissociation of the molecular bonds within tissue structures. This molecular dissociation is accompanied by the volumetric removal (i.e., ablative sublimation) of tissue and the production of low molecular weight gases, such as oxygen, nitrogen, carbon dioxide, hydrogen and methane. The short range of the accelerated charged particles within the tissue confines the molecular dissociation process to the surface layer to minimize damage and necrosis to the surrounding vessel wall 504. During the process, the gases may be aspirated through catheter 508. In addition, excess electrically conductive fluid, and other fluids (e.g., blood) may be aspirated from the target site to facilitate the surgeon's view.

Figure 15:
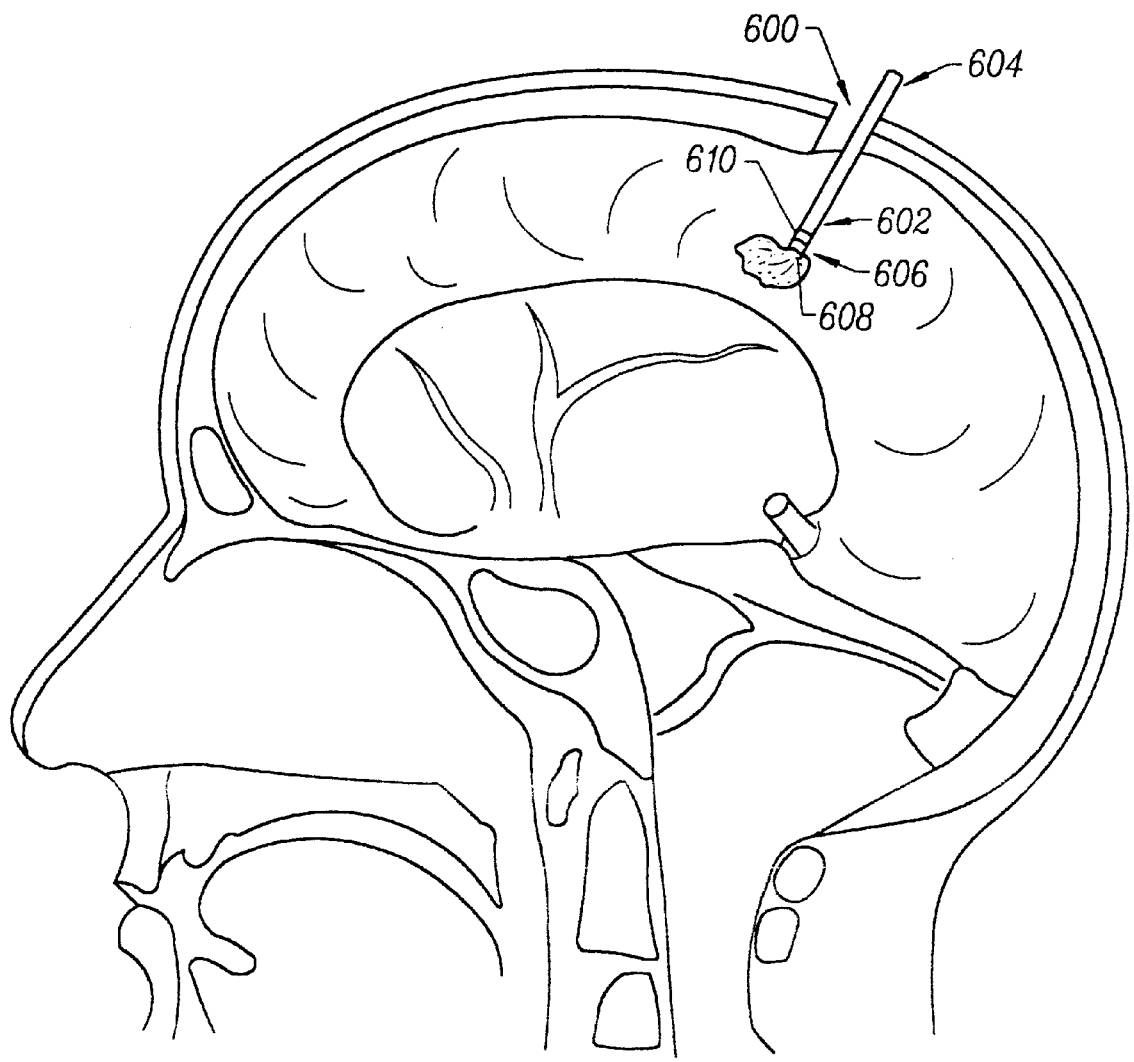
FIG. 15 is a sagittal section of the brain illustrating a method of removing a tumor according to the present invention.

FIG. 15 illustrates a method for removing a brain tumor according to the present invention. The system and method of the present invention is particularly useful in the ablation (i.e., disintegration) of cancer cells and tissue containing cancer cells, such malignant tumors within the brain and spinal cord, facial tumors, other tumors in the head and neck and the like. In particular, the ability to selective ablate tissue makes the present invention particularly useful for ablating tumors adjacent to or on nerves. In addition, the present invention's ability to completely disintegrate the target tissue can be advantageous in this application because simply vaporizing and fragmenting cancerous tissue (as with prior art devices) may lead to spreading of viable cancer cells (i.e., seeding) to other portions of the patient's body or to the surgical team in close proximity to the target tissue. In addition, the cancerous tissue can be removed to a precise depth while minimizing necrosis of the underlying tissue.

Figure 16:
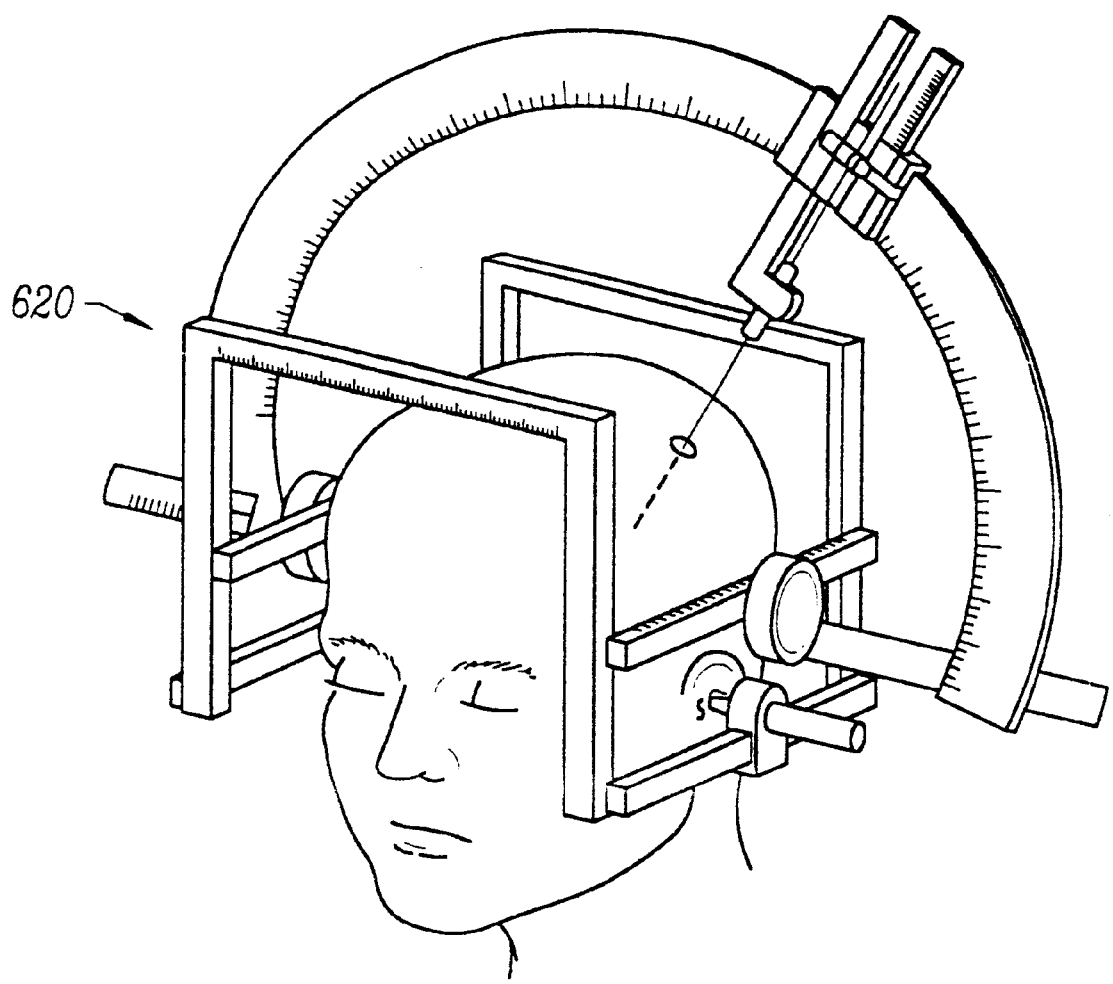
FIGS. 16 and 17 illustrate methods for performing the present invention in conjunction with frame and frameless sterotactic guiding methods.
Figure 17:
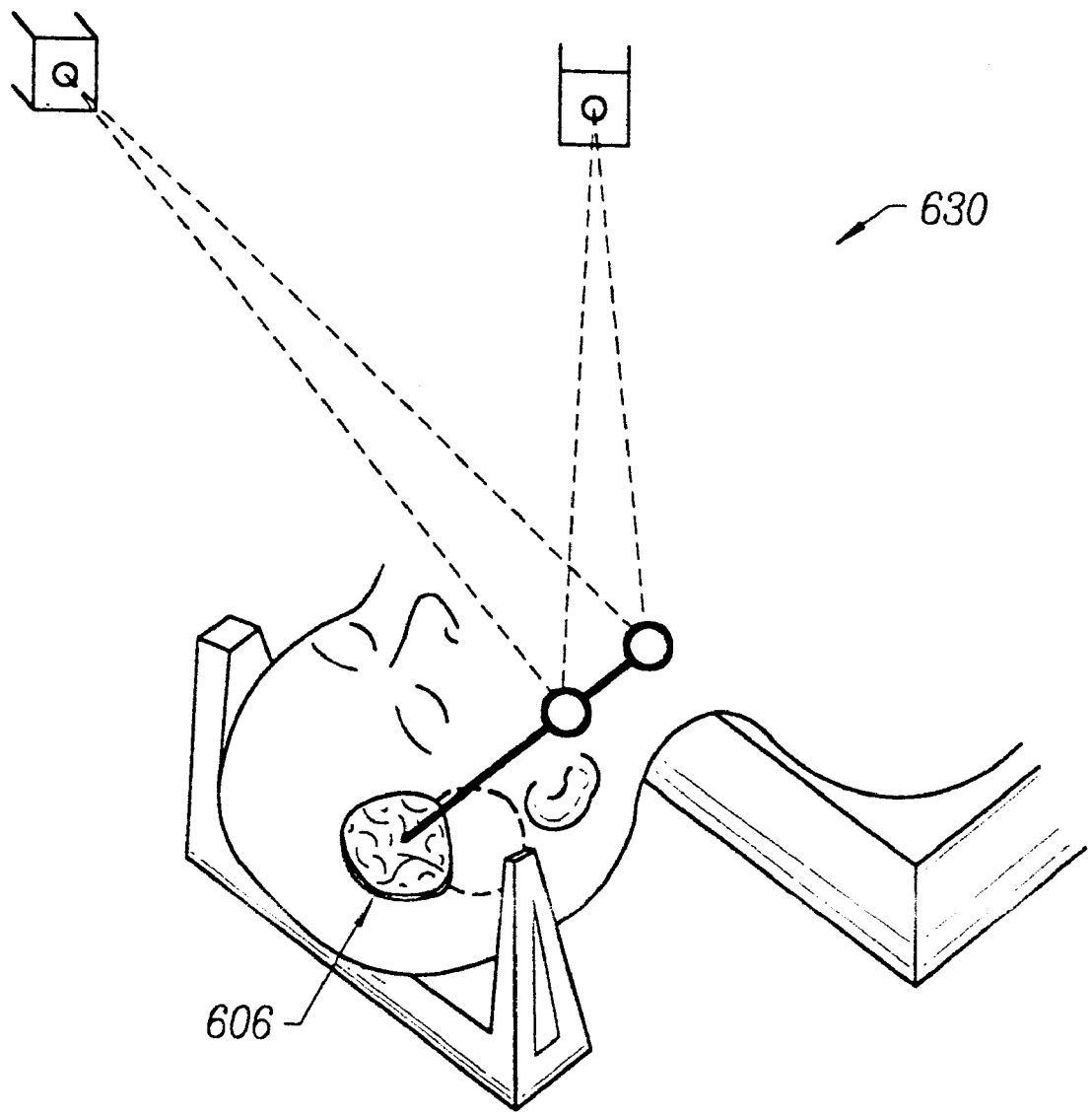

As shown in FIG. 15, a burr hole 600 is formed in the patient's skull to provide access to the brain. Of course, other methods of introduction may be used (e.g., craniectomy, transoral or transphenoidal routes). A working end 602 of an electrosurgical instrument 604 is guided to the tumor 606 with a conventional or non-conventional guiding system, such as a stereotactic frame 620 (FIG. 16) or an image guide system, such as frameless stereotaxy systems 630 (FIG. 17). Once the working end 602 of instrument 604 is positioned adjacent the tumor 606, electrically conductive fluid is delivered through one or more internal lumen(s) (not shown) within the instrument 604, and a high frequency voltage difference is applied between one or more electrode terminals 608 and a return electrode 610 on working end 602. As discussed above, the high frequency voltage is sufficient to convert the electrically conductive fluid (not shown) between the tumor 606 and electrode terminal(s) 522 into an ionized vapor layer or plasma (not shown), which results in the molecular dissociation of tumor tissue. Since the tumor cells are converted directly into non-viable gases, the spread of harmful tumor cells to other portions of the brain is minimized. During the process, the gases, excess electrically conductive fluid, and small non-ablated portions of the tumor tissue mass may be aspirated through catheter 508.

The present invention also provides systems and methods for treating aneurysms by applying RF energy to a hardenable substance, such as collagen. An aneurysm is a localized dilation of a blood vessel, typically an arterial blood vessel. If left untreated, the aneurysm generally becomes worse under the fluid pressure of blood flowing through the blood vessel, and eventually bursts or ruptures, with catastrophic results for the fluid-delivery capacity of the blood vessel. When the blood vessel is critical to the operation of the brain, this rupture is catastrophic for the patient.

One known method for treating intracranial aneurysms involves positioning small metallic coils into the bubble or pocket formed by the aneurysm outside of the main fluid flow of the blood vessel. Once present at the target site, the metallic coils fill the region defined by the aneurysm to mitigate or prevent the blood flow into this region, thereby limiting or preventing further enlargement of the aneurysm. While promising, this method may not be permanent as the aneurysm remains the weak area in the blood vessel wall, and thus may require further corrective action. In addition, this method is generally not effective with blood vessel walls that have not yet formed the bubble or pocket into which the small metallic coils would be inserted.

Figure 18:
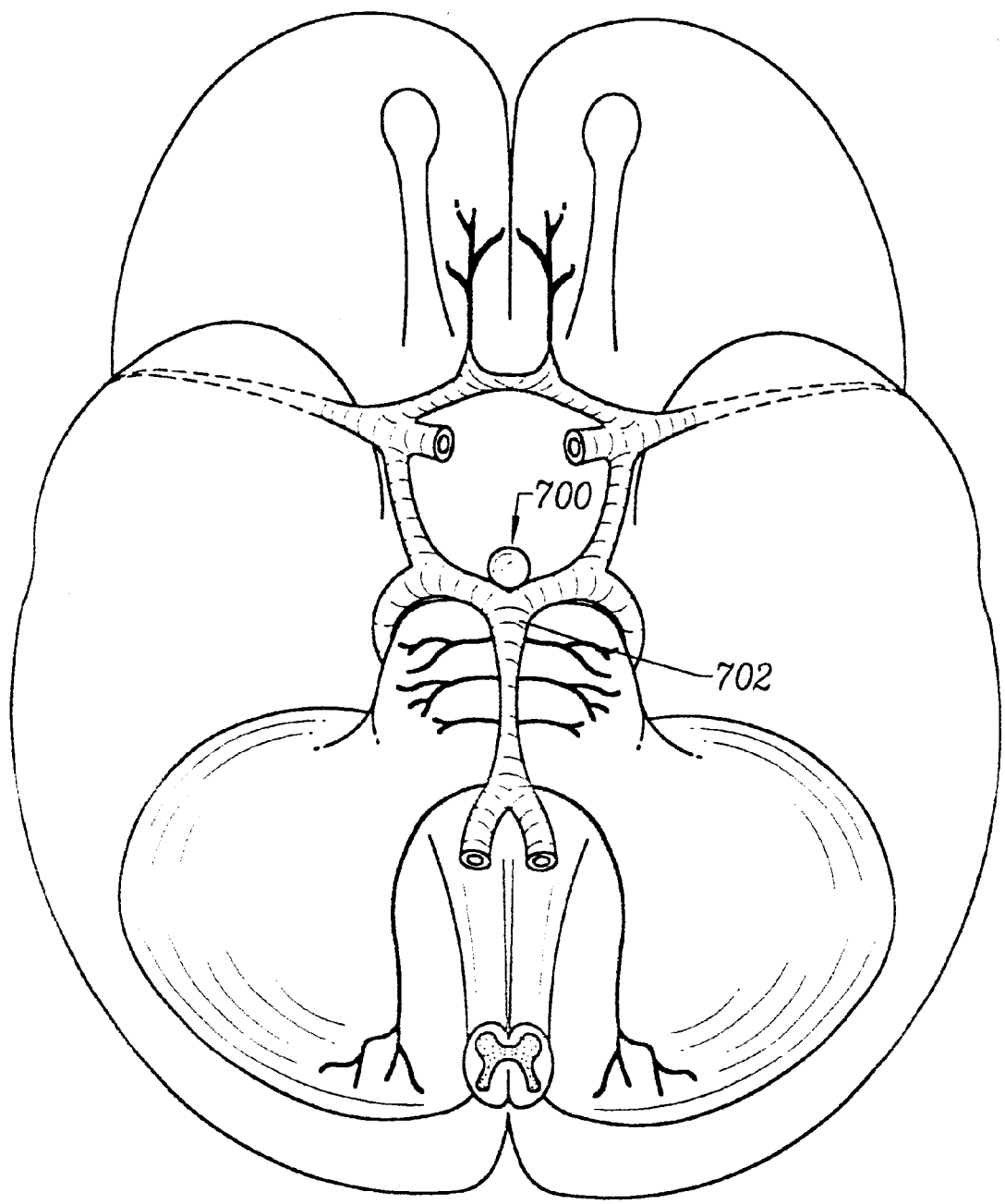
FIG. 18 illustrates a method of treating an aneurysm according to the present invention.

In this embodiment, a flowable substance, e.g., collagen, is delivered to the site of an aneurysm, and RF energy is applied to the substance to harden it to minimize or prevent enlargement of the aneurysm by blocking the flow of blood to the region of the aneurysm. FIG. 18 illustrates a saccular aneurysm 700 located in the posterior circulation between the basilar artery and the posterior inferior cerebella artery. According to the present invention, a working end of an electrosurgical catheter (not shown) is delivered through the patient's vasculature to the neck region 702 of the aneurysm 700. Collagen is then delivered through an internal lumen of the electrosurgical catheter (or through another catheter) to the neck region 702. It may be desirable to slow or stop the flow of blood (e.g., with a balloon) temporarily to facilitate placement of the collagen substance around the aneurysm 700. Once the collagen is in place, a high frequency voltage difference is applied between one or more electrode terminal(s) and one or more return electrodes on the working end of the catheter. In some embodiments, conductive fluid is delivered to the site to ensure a conductive path between the electrode terminal(s) and the return electrode(s). In other embodiments, the blood with the artery may be sufficient to provide this conductive path.

The energy supplied by the high frequency voltage is selected such that the collagen will harden in the region of the neck 702 of the aneurysm 700. The hardened collagen prevents further flow of blood into the fundus of the aneurysm, thereby limiting its growth. Of course it will be recognized that other substances besides collagen may be used in conjunction with the RF energy.

What is claimed is:

1. A method for treating a tumor located in the head and neck comprising:
    positioning an electrode terminal and a return electrode adjacent a body structure at a target site within a patient's head or neck;
    applying a sufficient high frequency voltage difference between the electrode terminal and the return electrode to volumetrically remove a portion of the body structure;
    effecting molecular dissociation of at least a portion of the cells within the tumor; and
    converting at least a portion of the tumor cells into non-viable gases to minimize the spread of the tumor.

2. The method of claim 1 wherein the body structure comprises an occlusive media disposed within a body vessel.

3. The method of claim 2 wherein the occlusive media is selected from the group comprising atheromatous occlusions, thrombotic occlusions, plaque and emboli.

4. The method of claim 2 further comprising applying high frequency voltage to the electrode terminal and a return electrode positioned within the blood vessel and spaced from the occlusive media such that an electrical current flows from the electrode terminal, through the region of the occlusive media, and to the return electrode.

5. The method of claim 4 wherein the high frequency voltage is applied in the presence of electrically conducting fluid, the method further comprising generating a current flow path through the electrically conducting fluid between the return electrode and the electrode terminal to selectively ablate the occlusive media.

6. The method of claim 1 further comprising:
    before the applying step, fluidly isolating a region around the occlusive media within the body passage to confine products of ablation within said region; and
    aspirating said ablation products from the body passage.

7. The method of claim 1 wherein the body structure comprises an arteriovenous malformation.

8. The method of claim 1 wherein the positioning step comprises advancing an electrosurgical instrument through a percutaneous penetration in the patient's head.

9. The method of claim 1 wherein the positioning step comprises advancing an electrosurgical catheter transluminally into the patient's head.

10. The method of claim 1 wherein the positioning step comprises the step of guiding the electrode terminal to the target site in the head.

11. The method of claim 10 further comprising an electrode array including a plurality of electrically isolated electrode terminals.

12. The method of claim 11 wherein the guiding step comprises detecting electrical properties of body structures adjacent each of the electrode terminals and guiding the electrode array to the target site based on the electrical properties.

13. The method of claim 12 wherein the electrical properties comprises impedance between each of the electrode terminals and the return electrode.

14. The method of claim 11 further comprising independently controlling current flow from at least two of the electrode terminals based on impedance between the electrode terminal and a return electrode.

15. The method of claim 1 wherein the electrode terminal comprises a single electrode at or near a distal end of an electrosurgical instrument.

16. The method of claim 1 wherein the return electrode and the electrode terminal are both located on an electrosurgical instrument.

17. The method of claim 1 further comprising positioning the electrode terminal and the return electrode within electrically conductive fluid.

18. The method of claim 17 further comprising applying sufficient voltage to the electrode terminal in the presence of the electrically conducting fluid to vaporize at least a portion of the fluid between the electrode terminal and the tissue structure.

19. The method of claim 18 further comprising accelerating charged particles from the vaporized fluid to the tissue structure to cause dissociation of the molecular bonds within the tissue structure.

20. The method of claim 17 further comprising positioning the electrode terminal and the return electrode within electrically conductive fluid to generate a current flow path between the return electrode and the electrode terminal.

21. A method for treating tissue in the head and neck comprising:
    positioning an electrode array including a plurality of electrically isolated electrode terminals and a return electrode adjacent a body structure at a target site within a patient's head or neck;

applying a sufficient high frequency voltage difference between the electrode terminals and the return electrode to volumetrically remove a portion of the body structure; and detecting electrical properties of body structures adjacent each of the electrode terminals and guiding the electrode array to the target site based on the electrical properties.

22. The method of claim 21 wherein the body structure comprises an occlusive media disposed within a body vessel.

23. The method of claim 22 wherein the occlusive media is selected from the group comprising atheromatous occlusions, thrombotic occlusions, plaque and emboli.

24. The method of claim 21 further comprising applying high frequency voltage to the electrode terminals and the return electrode positioned within the blood vessel and spaced from the occlusive media such that an electrical current flows from the electrode terminals, through the region of the occlusive media, and to the return electrode.

25. The method of claim 21 wherein the high frequency voltage is applied in the presence of electrically conducting fluid, the method further comprising generating a current flow path through the electrically conducting fluid between the return electrode and the electrode terminals to selectively ablate the occlusive media.

26. The method of claim 21 wherein the positioning step comprises advancing an electrosurgical instrument through a percutaneous penetration in the patient's head.

27. The method of claim 21 wherein the positioning step comprises advancing an electrosurgical catheter transluminally into the patient's head.

28. The method of claim 21 wherein the electrical properties comprises impedance between each of the electrode terminals and the return electrode.

29. The method of claim 21 wherein the return electrode and the electrode terminals are both located on an electrosurgical instrument.

* * * * *

UNITED STATES PATENT AND TRADEMARK OFFICE
CERTIFICATE OF CORRECTION

PATENT NO.         : 6,322,549 B1                                    Page 1 of 1
APPLICATION NO.    : 09/478729
DATED              : November 27, 2001
INVENTOR(S)        : Philip E. Eggers et al.

It is certified that error appears in the above-identified patent and that said Letters Patent is hereby corrected as shown below:

Title Page

(63) to correct the Related U.S. Application Data on the Title page of the patent, before the text "Continuation-in-part of application no. 09/026,851" the following should be inserted:
--Divisional of application no. 09/130,804 filed Aug. 7, 1998, now U.S. Patent No. 6,045,532, which is a--

Column 1, line 5, after the text "The present application", the following should be inserted:
--is a divisional of U.S. patent application no. 09/130,804 filed Aug. 7, 1998, now U.S. Patent No. 6,045,532, which--

Signed and Sealed this

Thirtieth Day of June, 2009

JOHN DOLL
*Acting Director of the United States Patent and Trademark Office*